United States Patent
Um et al.

(10) Patent No.: US 9,574,214 B2
(45) Date of Patent: Feb. 21, 2017

(54) ***PAENIBACILLUS* SP. CAA11 CAPABLE OF SACCHARIFICATION AND FERMENTATION OF CELLULOSE AND TRANSFORMED STRAIN THEREOF**

(71) Applicant: Korea Institute Of Science And Technology, Seoul (KR)

(72) Inventors: Youngsoon Um, Seoul (KR); Han Min Woo, Seoul (KR); Gyeongtaek Gong, Seoul (KR); Eun Sook Kim, Seoul (KR); Sukhyeong Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/088,935

(22) Filed: Apr. 1, 2016

(65) Prior Publication Data
US 2016/0289712 A1    Oct. 6, 2016

(30) Foreign Application Priority Data

Apr. 3, 2015  (KR) .................... 10-2015-0047444
Mar. 29, 2016 (KR) .................... 10-2016-0037650

(51) Int. Cl.

| | |
|---|---|
| *C12P 7/06* | (2006.01) |
| *C12N 9/24* | (2006.01) |
| *C12P 7/56* | (2006.01) |
| *C12R 1/01* | (2006.01) |
| *C12N 1/20* | (2006.01) |
| *C12N 1/22* | (2006.01) |
| *C12P 7/54* | (2006.01) |
| *C12P 7/40* | (2006.01) |
| *C12P 7/10* | (2006.01) |
| *C12N 9/42* | (2006.01) |

(52) U.S. Cl.
CPC . *C12P 7/56* (2013.01); *C12N 1/20* (2013.01); *C12N 1/22* (2013.01); *C12N 9/2437* (2013.01); *C12P 7/10* (2013.01); *C12P 7/40* (2013.01); *C12P 7/54* (2013.01); *C12R 1/01* (2013.01); *C12Y 302/01004* (2013.01)

(58) Field of Classification Search
CPC ............ C12P 7/06; C12P 2201/00; C12N 9/24
USPC ...................................... 435/252.3
See application file for complete search history.

(56) References Cited

U.S. PATENT DOCUMENTS

| 8,652,819 B2 | 2/2014 | Doran Peterson et al. |
| 2011/0081697 A1 | 4/2011 | Liu |

OTHER PUBLICATIONS

Linger, Jeffrey G., et al. "Heterologous Expression and Extracellular Secretion of Cellulolytic Enzymes by *Zymomonas mobilis*." Applied and Environmental Microbiology 76.19, 2010, (6360-6369).

Jung, Sang-Kyu, et al. "Heterologous Expression of Plant Cell Wall Degrading Enzymes for Effective Production of Cellulosic Biofuels." Journal of Biomedicine and Biotechnology, vol. 2012, Article ID 405842, 2012, (10 pages).

Tracy, Bryan P., et al. "Clostridia: the importance of their exceptional substrate and metabolite diversity for biofuel and biorefinery applications." Current Opinion in Biotechnology 23.3, 2012, (364-381).

Li, Lixiang, et al. "Efficient production of 2, 3-butanediol from corn stover hydrolysate by using a thermophilic *Bacillus licheniformis* strain." Bioresource Technology 170, 2014, (256-261).

*Primary Examiner* — Maryam Monshipouri
(74) *Attorney, Agent, or Firm* — NSIP Law

(57) ABSTRACT

The present disclosure relates to a novel strain capable of saccharifying and fermenting biomass-derived cellulose and a recombinant strain thereof with improved biomass saccharification capability. The present disclosure also relates to a method for producing a material useful as a bioenergy source material such as ethanol, acetic acid, formic acid, etc. using the strain or the recombinant strain. The strain or the recombinant strain may be usefully used in bioenergy industry.

20 Claims, 24 Drawing Sheets

A

PAENIBACILLUS SP. CAA11 CAPABLE OF SACCHARIFICATION AND FERMENTATION OF CELLULOSE AND TRANSFORMED STRAIN THEREOF

CROSS-REFERENCE TO RELATED APPLICATION

This application claims the priority of Korean Patent Application No. 10-2015-0047444, filed on Apr. 3, 2015 and Korean Patent Application No. 10-2016-0037650, filed on Mar. 29, 2016, and all the benefits accruing therefrom under 35 U.S.C. §119, the contents of which in its entirety are herein incorporated by reference.

BACKGROUND

1. Field

The present disclosure discloses a novel strain capable of saccharifying and fermenting biomass-derived cellulose and a genetically engineered strain thereof.

2. Description of the Related Art

Recently, studies on alternative energy are increasing because of the surge of oil prices and the restriction of fossil fuel use due to the obligation of implementing conventions on climate change. In particular, interests in renewable biomass are growing rapidly as energy production from biomass is expected to play an important role.

The processes using biomass include pretreatment, saccharification and fermentation processes. Biofuel is of low price competitiveness because of saccharifying enzymes used in the saccharification process are expensive.

Recently, many researches are focused on the development of an integrated biological process which allows saccharifying and fermenting of biomass at the same time by a single microorganism. For the development of the integrated biological process, a method of genetically engineering a saccharifying enzyme gene into monosaccharide-degrading *E. coli* or yeast is being studied. However, biofuel production is unsatisfactory because of low saccharification efficiency. For the development of microorganisms optimized for the development of the integrated biological process, improvement of saccharification capability through genetic engineering is necessary together with the securement of microorganisms capable of degrading polysaccharides, in addition to studies using monosaccharide-degrading microorganisms.

REFERENCES OF THE RELATED ART

Non-Patent Documents (Non-patent document 1) *Current Opinion in Biotechnology* (2012) 23:364.
(Non-patent document 2) *Applied and Environmental Microbiology* (2010) 76:6360.
(Non-patent document 3) *Journal of Biomedicine and Biotechnology* (2012) article ID 405842.

SUMMARY

The present disclosure is directed to providing a novel strain capable of producing a bioenergy source material effectively via a single process of saccharifying and fermenting biomass.

The present disclosure is also directed to providing a genetically engineered strain which has improved biomass saccharification capability over the novel strain.

In an aspect, the present disclosure provides *Paenibacillus* sp. CAA11 or a culture thereof.

In another aspect, the present disclosure provides a genetically engineered strain of *Paenibacillus* sp. CAA11, *Paenibacillus* sp. CAA11-Cel, which has been transformed by a vector containing the *Bacillus subtilis* 168 cellulase gene, and a culture thereof.

In another aspect, the present disclosure provides a method for preparing a genetically engineered strain of *Paenibacillus* sp. CAA11, *Paenibacillus* sp. CAA11-Cel, which includes: a step of preparing an expression vector by inserting a promoter into a shuttle vector; a step of preparing a recombinant vector by joining the promoter with a signal peptide and a cellulase-encoding gene by inserting them into the expression vector by overlap PCR and cloning the same; and a step of transforming the recombinant vector into *Paenibacillus* sp. CAA11.

In another aspect, the present disclosure provides a culturing method which includes culturing the *Paenibacillus* sp. CAA11 or the genetically engineered strain of *Paenibacillus* sp. CAA11, *Paenibacillus* sp. CAA11-Cel, in the presence of lignocellulosic biomass or cellulose and a method for producing a fermentation product which includes the same.

The novel strain *Paenibacillus* sp. CAA11 according to an exemplary embodiment of the present disclosure is capable of degrading cellulose without addition of an enzyme such as cellulase and can be cultured not only in anaerobic condition but also in aerobic condition.

The genetically engineered strain of *Paenibacillus* sp. CAA11 according to an exemplary embodiment of the present disclosure is capable of improving the biomass saccharification capability of *Paenibacillus* sp. CAA11 by overexpressing the saccharifying enzyme cellulase.

The *Paenibacillus* sp. CAA11 and the genetically engineered strain of *Paenibacillus* sp. CAA11 according to an exemplary embodiment of the present disclosure is not only capable of saccharifying cellulose but also capable of producing a bioenergy source material using a reducing sugar obtained therefrom such as glucose, xylose and cellobiose as a carbon source. Accordingly, they can be usefully applied to biomass, particularly lignocellulosic biomass. They can produce useful products such as formic acid, acetic acid, ethanol, etc. from the sugars produced by degrading biomass.

BRIEF DESCRIPTION OF THE DRAWINGS

FIG. 1*a* shows the cultured strain before staining with Congo red, and FIG. 1*b* shows the cultured strain after staining.

DETAILED DESCRIPTION

Figure 1A:
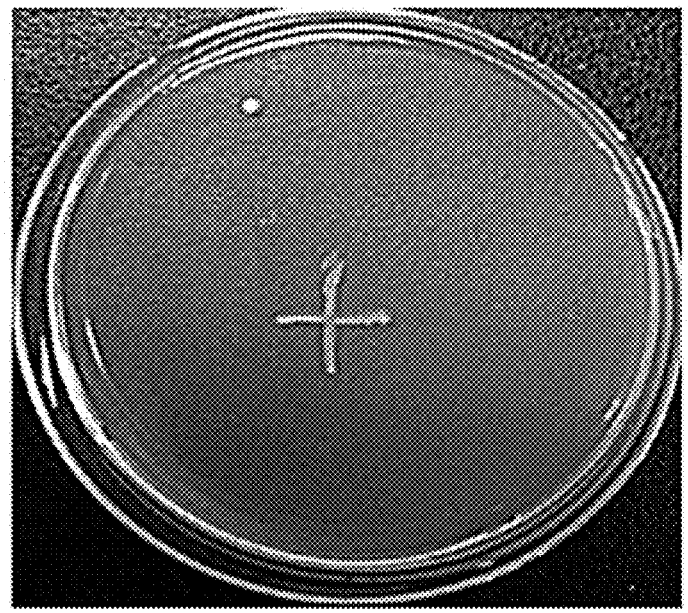
FIG. 1*a* and FIG. 1*b* show *Paenibacillus* sp. CAA11 cultured in a medium containing cellulose in order to investigate the cellulose-degrading activity of the strain.

In an aspect, the present disclosure relates to *Paenibacillus* sp. CAA11. The *Paenibacillus* sp. CAA11 strain has been isolated and identified by the inventors of the present disclosure for the first time. The inventors of the present disclosure have named the novel strain *Paenibacillus* sp. CAA11 and deposited it on Nov. 6, 2014 in the Korean Culture Center of Microorganisms with a deposition number of KCCM 11602P. Accordingly, in another aspect, the present disclosure relates to *Paenibacillus* sp. CAA11 with a deposition number of KCCM 11602P. In an aspect of the present disclosure, the *Paenibacillus* sp. CAA11 strain may contain a sequence of SEQ ID NO 3.

*Paenibacillus* is a rod-shaped Gram-positive bacterium. The *Paenibacillus* sp. CAA11 of the present disclosure is a novel strain in the genus *Paenibacillus* with a Genebank accession number KM275937. In general, a strain with a sequence similarity of 98% or smaller is classified as a novel strain. The *Paenibacillus* sp. CAA11 shows very low similarity of 97.01% as compared to *Paenibacillus barengoltzii* SAFN-016$^T$ and 96.16% as compared to *Paenibacillus phoenicis* 3PO2SA$^T$.

In another aspect, the present disclosure relates to a culture of *Paenibacillus* sp. CAA11 or *Paenibacillus* sp. CAA11 with a deposition number of KCCM 11602P. In another aspect, the present disclosure relates to a culturing method which includes culturing *Paenibacillus* sp. CAA11 or *Paenibacillus* sp. CAA11 with a deposition number of KCCM 11602P.

In the present disclosure, "culturing" is not particularly limited as long as it is performed by a culturing method well known in the art. A method of culturing a fermentation product obtained by culturing the strain first isolated and identified by the inventors of the present disclosure or culturing the strain is included without limitation. Specifically, the culturing of *Paenibacillus* sp. CAA11 in the present disclosure may be performed in the presence of sodium chloride, although not being limited thereto. In an aspect of the present disclosure, the concentration of the sodium chloride may be 0.1-10% (w/v), specifically 1-3% (w/v). However, the concentration of the sodium chloride is not limited thereto as long as the culturing of *Paenibacillus* sp. CAA11 is possible.

In an aspect, the culturing of *Paenibacillus* sp. CAA11 in the present disclosure may be performed at pH 5.5-8 and/or at 25-45° C., although not being limited thereto. Under this condition, better growth of the strain and production of byproducts can be observed. In this aspect, the culturing of *Paenibacillus* sp. CAA11 in the present disclosure may be performed at pH 5.5-8, pH 5.7-7.8, pH 5.9-7.6, pH 6.1-7.4 or pH 6.3-7.2 and/or at 26-44° C., 27-43° C., 28-42° C., 29-41° C. or 30-40° C., although not being limited thereto.

In another aspect, the present disclosure relates to a culturing method which includes culturing *Paenibacillus* sp. CAA11 or *Paenibacillus* sp. CAA11 with a deposition number of KCCM 11602P in aerobic or anaerobic condition in the presence of lignocellulosic biomass or cellulose. In an aspect, the "culturing" in the present disclosure may be performed in both aerobic and anaerobic conditions, although not being limited thereto.

Because most of the bacteria known to degrade cellulose such as *Clostridium thermocellum*, *Clostridium cellulovorans*, etc. are anaerobic bacteria, it is difficult to culture them. Accordingly, there have been many limitations in genetic modification thereof. However, the *Paenibacillus* sp. CAA11 according to an aspect of the present disclosure can be cultured not only in anaerobic condition but also in aerobic condition and a bioenergy source material such as formic acid, acetic acid, ethanol, etc. can be produced from a culture thereof. That is to say, the *Paenibacillus* sp. CAA11 can quickly respond to the change in dissolved oxygen condition or redox condition and degrade cellulose. In an exemplary embodiment, acetic acid can be produced by culturing the *Paenibacillus* sp. CAA11 in aerobic condition and formic acid, acetic acid or ethanol can be produced by culturing the *Paenibacillus* sp. CAA11 in anaerobic condition.

In another aspect, the present disclosure relates to a method for producing a fermentation product, which includes culturing *Paenibacillus* sp. CAA11 or *Paenibacillus* sp. CAA11 with a deposition number of KCCM 11602P. The term "fermentation product" is used in the broadest sense, including not only a product obtained by culturing or fermenting the novel strain of the present disclosure but also a substance obtained by culturing a microorganism genetically modified from the novel strain. For example, the produced fermentation product may be a source material from which bioenergy can be produced. In an aspect, the producing method may include culturing the *Paenibacillus* sp. CAA11 in the presence of lignocellulosic biomass or cellulose. Specifically, the producing method may include producing one or more of glucose, xylose and cellobiose by degrading lignocellulosic biomass or cellulose with the *Paenibacillus* sp. CAA11 and then culturing the *Paenibacillus* sp. CAA11 by using one or more of the produced glucose, xylose and cellobiose. In another aspect, the culturing may be performed under anaerobic or aerobic condition.

In another aspect, the present disclosure relates to a method for producing formic acid, which includes culturing Paenibacillus sp. CAA11 or Paenibacillus sp. CAA11 with a deposition number of KCCM 11602P in the presence of cellulose. In another aspect, the present disclosure relates to a method for producing acetic acid, which includes culturing Paenibacillus sp. CAA11 in the presence of cellulose. In another aspect, the present disclosure relates to a method for producing ethanol, which includes culturing Paenibacillus sp. CAA11 in the presence of cellulose.

In the present disclosure, each of the formic acid, the acetic acid and the ethanol is used as a bioenergy source material and may mean bio-formic acid, bio-acetic acid or bioethanol derived from biomass.

In accordance with a method according to an aspect of the present disclosure, because a bioenergy source material can be produced using a reducing sugar obtained as a result of the cellulase activity of Paenibacillus sp. CAA11 or Paenibacillus sp. CAA11 with a deposition number of KCCM 11602P, both the saccharification of lignocellulosic biomass-derived cellulose and the fermentation of the reducing sugar can be achieved simply by culturing the strain. Therefore, addition of cellulase is not necessary in the present disclosure and the bioenergy source material such as formic acid, acetic acid and ethanol can be obtained more conveniently and economically. Accordingly, the present disclosure can be very useful in the production of eco-friendly bioenergy.

In another aspect, the present disclosure relates to a method for producing bioenergy, which includes producing bioenergy using a byproduct obtained by culturing Paenibacillus sp. CAA11 or Paenibacillus sp. CAA11 with a deposition number of KCCM 11602P in the presence of cellulose as described above. In an aspect, the byproduct may include one or more selected from a group consisting of acetic acid, formic acid and ethanol. The bioenergy means energy obtained from biomass as a fuel. It includes any energy produced using a fermentation product obtained by the method according to an aspect of the present disclosure, such as acetic acid, formic acid and/or ethanol, etc., without particular limitation. Any method of producing bioenergy using a fermentation product such as acetic acid, formic acid and/or ethanol, etc., which is well known in the art, may be used without limitation.

In another aspect, the present disclosure relates to a medium containing sodium chloride as a medium for culturing Paenibacillus sp. CAA11 or Paenibacillus sp. CAA11 with a deposition number of KCCM 11602P.

In another aspect, the present disclosure relates to a genetically engineered strain of Paenibacillus sp. CAA11, which has been transformed by a vector containing the Bacillus subtilis 168 cellulase gene.

In another aspect, the present disclosure relates to a culture of a genetically engineered strain of Paenibacillus sp. CAA11, which has been transformed by a vector containing the Bacillus subtilis 168 cellulase gene.

In an aspect of the present disclosure, the genetically engineered strain of Paenibacillus sp. CAA11 may be Paenibacillus sp. CAA11-Cel, a genetically engineered strain of Paenibacillus sp. CAA11 with a deposition number of KCCM11825P.

In another aspect, the present disclosure relates to a method for preparing the genetically engineered strain of Paenibacillus sp. CAA11, which includes: a step of preparing an expression vector by inserting a promoter into a shuttle vector; a step of preparing a recombinant vector by joining the promoter with a signal peptide and a cellulase-encoding gene by inserting them into the expression vector by overlap PCR and cloning the same; and a step of transforming the recombinant vector into Paenibacillus sp. CAA11.

Specifically, the method according to an aspect of the present disclosure may include: a step of establishing a method for transforming Paenibacillus sp. CAA11; a step of screening a potent promoter that can overexpress a target protein in Paenibacillus sp. CAA11 when inserted into a shuttle vector for E. coli and Bacillus; and a step of inserting the selected promoter into a shuttle vector for E. coli and Bacillus and then preparing a recombinant vector by cloning the endocellulase cel5 of Bacillus subtilis 168.

In an aspect, the expression vector used in the present disclosure may contain a promoter, a target gene and a terminator sequence. The expression vector may contain an antibiotic resistance gene commonly used in the art as a selection marker. For example, it may contain a resistance gene against ampicillin, gentamicin, carbenicillin, streptomycin, kanamycin, geneticin, neomycin, tetracycline, etc. In another aspect, the expression vector contains a promoter sequence, a nucleotide sequence of a gene to be expressed and a terminator sequence and these sequences may be joined in that order from 5' to 3' end.

In an aspect of the present disclosure, the gene to be expressed may be the cellulase-encoding gene, e.g., the cel5 gene. The gene is introduced into the expression vector and is expressed in Paenibacillus sp. CAA11. In an exemplary embodiment of the present disclosure, the cel5 gene may be the cel5 gene of Bacillus subtilis 168 and may contain a nucleotide sequence of SEQ ID NO 4. In an exemplary embodiment, the recombinant vector may contain a promoter having a nucleotide sequence of SEQ ID NO 5 upstream of the Bacillus subtilis 168 cellulase gene. Also, in an exemplary embodiment, the recombinant vector may have a nucleotide sequence of SEQ ID NO 6.

SEQ ID NO 4

```
gcagggacaaaaacgccagtagccaagaatggccagcttagcataaaaggtacacagctcgttaaccgag acggtaaagcggtacagctgaaggggatcagttcacacggattgcaatggtatggagaatatgtcaataaagacagctt aaaatggctgagagatgattggggtatcaccgttttccgtgcagcgatgtatacggcagatggcggttatattgacaacccg tccgtgaaaaataaagtaaaagaagcggttgaagcggcaaaagagcttgggatatatgtcatcattgactggcatatctta aatgacggtaatccaaaccaaataaagagaaggcaaaagaattcttcaaggaaatgtcaagcctttacggaaacacg ccaaacgtcatttatgaaattgcaaacgaaccaaacggtgatgtgaactggaagcgtgatattaaaccatatgcggaaga agtgatttcagttatccgcaaaaatgatccagacaacatcatcattgtcggaaccggtacatggagccaggatgtgaatga tgctgccgatgaccagctaaaagatgcaaacgttatgtacgcacttcattttatgccggcacacacggccaattttacggg ataaagcaaactatgcactcagcaaaggagcacctattttgtgacagagtggggaacaagcgacgcgtctggcaatgg
```

-continued cggtgtattccttgatcaatcgagggaatggctgaaatatctcgacagcaagaccattagctgggtgaactggaatctttctg ataagcaggaatcatcctcagctttaaagccgggggcatctaaaacaggcggctggcggttgtcagatttatctgcttcagg aacattcgttagagaaaacattctcggcaccaaagattcgacgaaggacattcctgaaacgccatcaaaagataaaccc acacaggaaaatggtatttctgtacagtacagagcagggatgggagtatgaacagcaaccaaatccgtccgcagcttc aaataaaaaataacggcaataccacggttgatttaaaagatgtcactgcccgttactggtataaagcgaaaaacaaagg ccaaaactttgactgtgactacgcgcagattggatgcggcaatgtgacacacaagtttgtgacgttgcataaaccaaagc aaggtgcagatacctatctggaacttggatttaaaaacggaacgttggcaccgggagcaagcacagggaatattcagct ccgtcttcacaatgatgactggagcaattatgcacaaagcggcgattattccttttttcaaatcaaatacgtttaaaacaacga aaaaaatcacattatatgatcaaggaaaactgatttggggaacagaaccaaa

SEQ ID NO 5 tgataggtggtatgttttcgcttgaacttttaaatacagccattgaacatacggttgatttaataactgacaaacatca ccctcttgctaaagcggccaaggacgctgccgccggggctgtttgcgttttgccgtgatttcgtgtatcattggtttacttattttttt tgccaaagctgtaatggctgaaaattcttacatttattttacattttagaaatgggcgtgaaaaaaagcgcgcgattatgtaa aatataaagtgatagcggatcctgataggtggtatgttttcgcttgaacttttaaatacagccattgaacatacggttgatttaat aactgacaaacatcaccctcttgctaaagcggccaaggacgctgccgccggggctgtttgcgttttgccgtgatttcgtgta tcattggtttacttattttttgccaaagctgtaatggctgaaaattcttacatttattttacattttagaaatgggcgtgaaaaaaa gcgcgcgattatgtaaaatataaagtgatagc

SEQ ID NO 6 aattcgagctctgataggtggtatgttttcgcttgaacttttaaatacagccattgaacatacggttgatttaataactg acaaacatcaccctcttgctaaagcggccaaggacgctgccgccggggctgtttgcgttttgccgtgatttcgtgtatcattg gtttacttattttttgccaaagctgtaatggctgaaaattcttacatttattttacattttagaaatgggcgtgaaaaaaagcgcg cgattatgtaaaatataaagtgatagcggatcctgataggtggtatgttttcgcttgaacttttaaatacagccattgaacatac ggttgatttaataactgacaaacatcaccctcttgctaaagcggccaaggacgctgccgccggggctgtttgcgttttgccg tgatttcgtgtatcattggtttacttattttttgccaaagctgtaatggctgaaaattcttacatttattttacattttagaaatgggcg tgaaaaaaagcgcgcgattatgtaaaatataaagtgatagcggtaccattataggtaagagaggaatgtacacatgcgc aacttgaccaagacatctctattactggccggcttatgcatagcggcccaaatggtttttgtaacacatgcccagctgcagg gacaaaaacgccagtagccaagaatggccagcttagcataaaaggtacacagctcgttaaccgagacggtaaagcgg tacagctgaaggggatcagttcacacggattgcaatggtatggagaatatgtcaataaagacagcttaaaatggctgaga gatgattggggtatcaccgttttccgtgcagcgatgtatacggcagatggcggttatattgacaacccgtccgtgaaaaata aagtaaaagaagcggttgaagcggcaaaagagcttgggatatatgtcatcattgactggcatatcttaaatgacggtaatc caaaccaaaataaagagaaggcaaaagaattcttcaaggaaatgtcaagcctttacggaaacacgccaaacgtcattt atgaaattgcaaacgaaccaaacggtgatgtgaactggaagcgtgatattaaaccatatgcggaagaagtgatttcagtt atccgcaaaaatgatccagacaacatcatcattgtcggaaccggtacatggagccaggatgtgaatgatgctgccgatg accagctaaaagatgcaaacgttatgtacgcacttcattttatgccggcacacacggccaattttacgggataaagcaaa ctatgcactcagcaaaggagcacctattttttgtgacagagtggggaacaagcgacgcgtctggcaatggcggtgtattcctt gatcaatcgagggaatggctgaaatatctcgacagcaagaccattagctgggtgaactggaatctttctgataagcagga atcatcctcagctttaaagccgggggcatctaaaacaggcggctggcggttgtcagatttatctgcttcaggaacattcgtta gagaaaacattctcggcaccaaagattcgacgaaggacattcctgaaacgccatcaaaagataaacccacacaggaa aatggtatttctgtacagtacagagcagggatgggagtatgaacagcaaccaaatccgtccgcagcttcaaataaaaa ataacggcaataccacggttgatttaaaagatgtcactgcccgttactggtataaagcgaaaaacaaaggccaaaacttt gactgtgactacgcgcagattggatgcggcaatgtgacacacaagtttgtgacgttgcataaaccaaagcaaggtgcag -continued

```
atacctatctggaacttggatttaaaaacggaacgttggcaccgggagcaagcacagggaatattcagctccgtcttcaca
atgatgactggagcaattatgcacaaagcggcgattattccttttcaaatcaaatacgtttaaaacaacgaaaaaaatcac
attatatgatcaaggaaaactgatttggggaacagaaccaaatcatcatcatcatcattagtctagagtcgacctgcag
gcatgcaagcttggcgtaatcatggtcatagctgtttcctgtgtgaaattgttatccgctcacaattccacacaacatacgagc
cggaagcataaagtgtaaagcctggggtgcctaatgagtgagctaactcacattaattgcgttgcgctcactgcccgctttc
cagtcgggaaacctgtcgtgccagcccttcaaacttcccaaaggcgagccctagtgacattagaaaaccgactgtaaaa
agtacagtcggcattatctcatattataaaagccagtcattaggcctatctgacaattcctgaatagagttcataaacaatcct
gcatgataaccatcacaaacagaatgatgtacctgtaaagatagcggtaaatatattgaattacctttattaatgaattttcctg
ctgtaataatgggtagaaggtaattactattattattgatatttaagttaaacccagtaaatgaagtccatggaataatagaaa
gagaaaaagcattttcaggtataggtgttttgggaaacaatttccccgaaccattatatttctacatcagaaaggtataaat
cataaaactctttgaagtcattctttacaggagtccaaataccagagaatgttttagatacaccatcaaaaattgtataaagtg
gctctaacttatcccaataacctaactctccgtcgctattgtaaccagttctaaaagctgtatttgagtttatcacccttgtcacta
agaaataaatgcagggtaaaatttatatccttcttgttttatgtttcggtataaaacactaatatcaatttctgtggttatactaaa
agtcgtttgttggttcaaataatgattaaatatctcttttctcttccaattgtctaaatcaattttattaaagttcatttgatatgcctcct
aaattttatctaaagtgaatttaggaggcttacttgtctgctttcttcattagaatcaatcctttttaaaagtcaatcccgtttgttga
actactctttaataaaataattttccgttcccaattccacattgcaataatagaaaatccatcttcatcggcttttttcgtcatcatct
gtatgaatcaaatcgccttcttctgtgtcatcaaggtttaattttttatgtatttcttttaacaaaccaccataggagattaaccttta
cggtgtaaaccttcctccaaatcagacaaacgtttcaaattcttttcttcatcatcggtcataaaatccgtatcctttacaggata
ttttgcagtttcgtcaattgccgattgtatatccgatttatatttattttcggtcgaatcatttgaacttttacatttggatcatagtctaa
tttcattgccttttccaaaattgaatccattgttttgattcacgtagttttctgtattcttaaaataagttggttccacacataccaat
acatgcatgtgctgattataagaattatctttattatttattgtcacttccgttgcacgcataaaaccaacaagatttttattaattttt
tatattgcatcattcggcgaaatccttgagccatatctgacaaactcttatttaattcttcgccatcataaacattttaactgttaat
gtgagaaacaaccaacgaactgttggcttttgtttaataacttcagcaacaaccttttgtgactgaatgccatgtttcattgctct
cctccagttgcacattggacaaagcctggatttacaaaaccacactcgatacaactttctttcgcctgtttcacgattttgtttata
ctctaatatttcagcacaatcttttactctttcagcctttttaaattcaagaatatgcagaagttcaaagtaatcaacattagcgatt
ttcttttctctccatggtctcacttttccactttttgtcttgtccactaaaacccttgattttcatctgaataaatgctactattaggaca
cataatattaaaagaaaccccatctatttagttatttgtttggtcacttataacttaacagatgggtttttctgtgcaaccaattt
taagggttttcaatactttaaaacacatacataccaacacttcaacgcacctttcagcaactaaaataaaaatgacgttatttc
tatatgtatcaagaatagaaagaactcgtttttcgctacgctcaaaacgcaaaaaaagcactcattcgagtgcttttttcttatc
gctccaaatcatgcgattttttcctctttgcttttctttgctcacgaagttctcgatcacgctgcaaaacatcttgaagcgaaaaa
gtattcttcttttcttccgatcgctcatgctgacgcacgaaaagccctctaggcgcataggaacaactcctaaatgcatgtgag
gggttttctcgtccatgtgaacagtcgcatacgcaatattttgtttcccatactgcattaatgaatcggccaacgcgcgggag
aggcggtttgcgtattgggcgctcttccgcttcctcgctcactgactcgctgcgctcggtcgttcggctgcggcgagcggtatc
agctcactcaaaggcggtaatacggttatccacagaatcaggggataacgcaggaaagaacatgtgagcaaaaggcc
agcaaaaggccaggaaccgtaaaaaggccgcgttgctggcgtttttccataggctccgcccccctgacgagcatcacaa
aaatcgacgctcaagtcagaggtggcgaaacccgacaggactataaagataccaggcgtttccccctggaagctccctc
gtgcgctctcctgttccgaccctgccgcttaccggatacctgtccgcctttctcccttcgggaagcgtggcgctttctcatagctc
acgctgtaggtatctcagttcggtgtaggtcgttcgctccaagctgggctgtgtgcacgaaccccccgttcagcccgaccgc
tgcgccttatccggtaactatcgtcttgagtccaacccggtaagacacgacttatcgccactggcagcagccactggtaac
aggattagcagagcgaggtatgtaggcggtgctacagagttcttgaagtggtggcctaactacggctacactagaagaac
agtatttggtatctgcgctctgctgaagccagttaccttcggaaaaagagttggtagctcttgatccggcaaacaaaccacc
```

-continued

```
gctggtagcggtggttttttgtttgcaagcagcagattacgcgcagaaaaaaggatctcaagaagatcctttgatcttttcta cggggtctgacgctcagtggaacgaaaactcacgttaagggattttggtcatgagattatcaaaaaggatcttcacctagat cctttttaaattaaaaatgaagttttaaatcaatctaaagtatatatgagtaaacttggtctgacagttaccaatgcttaatcagtg aggcacctatctcagcgatctgtctatttcgttcatccatagttgcctgactccccgtcgtgtagataactacgatacgggagg gcttaccatctggcccagtgctgcaatgataccgcgagacccacgctcaccggctccagatttatcagcaataaaccag ccagcccgatatgggaaacaaaatattgcgtatgcgactgttcacatggacgagaaaaccccctcacatgcatttaggagtt gttcctatgcgcctagagggcttttcgtgcgtcagcatgagcgatcggaagaaaagaagaatacttttttcgcttcaagatgttt tgcagcgtgatcgagaacttcgtgagcaaagaaaagcaaagaggaaaaaatcgcatgatttggagcgataagaaaaa gcactcgaatgagtgctttttttgcgttttgagcgtagcgaaaaacgagttctttctattcttgatacatatagaaataacgtcattt ttattttagttgctgaaaggtgcgttgaagtgttggtatgtatgtgattcaataatttcttttactcgctcgttatagtcgatcggttcat cattcaccaaatcataattttcatgtgaccgttctttatcaatatcgggattcgttttactttcccgttctctctgattgtgaaattg
```

20

In an aspect of the present disclosure, the step of preparing the recombinant vector may be accomplished by inserting the potent promoter and the cellulase-encoding gene into the expression vector by PCR and cloning the same.

In an aspect of the present disclosure, the transformed *Paenibacillus* sp. CAA11 may be prepared as a competent cell. In an exemplary embodiment, a step of preparing the competent cell may include: a step of culturing *Paenibacillus* sp. CAA11 in an LB (Luria-Bertani), 0.5 M sorbitol medium at 37° C. overnight; a step of subculturing *Paenibacillus* sp. CAA11 in the LB, 0.5 M sorbitol medium and harvesting the strain by centrifuging at 6000 rpm for 10 minutes at 4° C. when $OD_{600}$ reaches 0.8; a step of washing 4 times with 30 mL of a cold washing buffer (0.5 M sorbitol, 0.5 M mannitol, 0.25 mM $KH_2PO_4$, 0.25 mM $K_2HPO_4$, 0.5 mM $MgCl_2$, 10% glycerol); and a step of resuspending in a washing buffer with a volume of 1/40 as compared to that of the culture and then storing at −70° C.

In another aspect of the present disclosure, the transformation step may further include an electroporation step.

In an aspect, the electroporation step may include: a step of mixing 300-400 ng of purified plasmid DNA and 60 μL of the cold cell suspension and transferring to an electroporation cuvette which has been cooled to a very low temperature; a step of conducting electroporation under a condition of 21 kV/cm, 200Ω and 25 μF (time constant=5 ms); mixing 1 mL of an LB, 0.5 M sorbitol, 0.38 M mannitol medium with pulsed cells and culturing them at 37° C. for 3 hours while agitating at 200 rpm; and a step of spreading the cell mixture.

The genetically engineered strain of *Paenibacillus* sp. CAA11 prepared according to an aspect of the present disclosure, which has been transformed by a recombinant vector containing the cellulase gene, can overexpress cellulase. Accordingly, when the genetically engineered strain of *Paenibacillus* sp. CAA11 is cultured in a cellulose medium, the production of formic acid, acetic acid and ethanol can be increased due to the cellulase overexpression.

Accordingly, in another aspect, the present disclosure relates to a culturing method which includes culturing the genetically engineered strain of *Paenibacillus* sp. CAA11 in the presence of lignocellulosic biomass or cellulose. Specifically, the genetically engineered strain of *Paenibacillus* sp. CAA11 may be cultured in the presence of cellulose. In an exemplary embodiment, the genetically engineered strain of *Paenibacillus* sp. CAA11 may be cultured by the culturing method of *Paenibacillus* sp. CAA11 described above without any limitation.

In another aspect, the present disclosure relates to a method for producing a fermentation product, which includes a step of culturing the genetically engineered strain of *Paenibacillus* sp. CAA11 with the deposition number KCCM11825P, *Paenibacillus* sp. CAA11-Cel. In an aspect, the producing method may include culturing the genetically engineered strain of *Paenibacillus* sp. CAA11 in the presence of lignocellulosic biomass or cellulose. In another aspect, the culturing may be performed in anaerobic or aerobic condition. In an exemplary embodiment, the method for producing a fermentation product using the genetically engineered strain of *Paenibacillus* sp. CAA11 may be the method for producing a fermentation product using *Paenibacillus* sp. CAA11 described above without any limitation.

In an aspect, the step of culturing the *Paenibacillus* sp. CAA11 or the genetically engineered strain of *Paenibacillus* sp. CAA11 may include culturing the *Paenibacillus* sp. CAA11 or the genetically engineered strain of *Paenibacillus* sp. CAA11 in a medium containing cellulose as a carbon source, yeast extract as a nitrogen source, etc. In an exemplary embodiment, the cellulose may be one obtained by decrystallizing crystalline cellulose by treating with 85% phosphoric acid at 50° C. for 6 hours.

In an aspect, the method for producing a fermentation product may include producing one or more of glucose, xylose and cellobiose by degrading lignocellulosic biomass or cellulose with the genetically engineered strain of *Paenibacillus* sp. CAA11 and then culturing the genetically engineered strain of *Paenibacillus* sp. CAA11 by using one or more of the produced glucose, xylose and cellobiose.

In an aspect, the fermentation product may include one or more selected from a group consisting of formic acid, acetic acid and ethanol. Because the genetically engineered strain of *Paenibacillus* sp. CAA11 is one in which cellulase is overexpressed using *Paenibacillus* sp. CAA11 which is capable of degrading polysaccharides, production of useful products such as formic acid, acetic acid, ethanol, from the polysaccharide cellulose can be enhanced.

In order to degrade the polysaccharide cellulose, various saccharifying enzymes such as endocellulase, exocellulase, β-glucosidase, etc may be used. Among them, cel5, the endocellulase of *Bacillus subtilis* 168, is known to exhibit high activity in *Bacillus subtilis* 168.

Accordingly, in another aspect, the present disclosure relates to a method for producing bioenergy, which includes: a step of culturing the genetically engineered strain of *Paenibacillus* sp. CAA11 in the presence of lignocellulosic biomass or cellulose; and a step of producing bioenergy using a byproduct obtained during the culturing. The byproduct may be one or more selected from a group consisting of acetic acid, formic acid and ethanol. In an exemplary embodiment, the method for producing bioenergy using the genetically engineered strain of *Paenibacillus* sp. CAA11 may be the same as the method for producing bioenergy using *Paenibacillus* sp. CAA11 described above without any limitation. Because the genetically engineered strain of *Paenibacillus* sp. CAA11 overexpresses cel5, which is the endocellulase of *Bacillus subtilis* 168, it can produce useful products such as formic acid, acetic acid, ethanol, etc. more effectively.

Formic acid is widely used as a preservative and is also used industrially in the production of leather and as a coagulant in the production of rubber. Formic acid is also being investigated for use in fuel cells. Acetic acid is widely used industrially in the preparation of vinyl acetate, dyes, synthetic vinegar, medicines such as aspirin, acetate esters, acetic anhydride, acetone, etc. Ethanol is an important raw material in chemical synthesis and is drawing a lot of attractions as a biofuel.

Hereinafter, the present disclosure will be described in detail through examples. However, the following examples are for illustrative purposes only and it will be apparent to those of ordinary skill in the art that the scope of the present disclosure is not limited by the examples.

Example 1

Isolation of Cellulose-Degrading Bacterium *Paenibacillus* sp. CAA11

Example 1-1

Harvesting of Strains

In order to isolate a strain that can produce chemicals directly using cellulose, soil samples taken from cellulose-rich environments such as Dongmak Beach, Mt. Gwanak and Mt. Jiri of Korea and Indonesia were plated onto plate media containing 10 g/L cellulose. After culturing overnight at 37° C. in an incubator, the cultured strains were screened primarily. The purified and isolated strains were cultured again in cellulose media and screened secondarily by investigating whether the isolated strains can degrade cellulose through Congo red staining and destaining. The composition of the medium for culturing the isolated strains is shown in Tables 1 and 2.

TABLE 1

| Medium composition | g/L |
| --- | --- |
| $K_2HPO_4$ | 5 |
| $KH_2PO_4$ | 3 |
| $(NH_4)_2SO_4$ | 2 |
| $MgSO_4 \cdot 7H_2O$ | 0.4 |
| Peptone | 0.5 |
| Beef extract | 0.3 |
| Yeast extract | 1 |
| $CaCl_2 \cdot 2H_2O$ | 0.1 |

TABLE 1-continued

| Medium composition | g/L |
| --- | --- |
| Trace elements | 1 mL |
| Cellulose | 10 |

TABLE 2

| Trace elements | |
| --- | --- |
| HCl | 1 ml/L |
| $ZnCl_2$ | 70 mg/L |
| $MnCl_2 \cdot 4H_2O$ | 100 mg/L |
| $H_3BO_3$ | 60 mg/L |
| $CoCl_2 \cdot 6H_2O$ | 200 mg/L |
| $CuCl_2 \cdot 2H_2O$ | 20 mg/L |
| $NiCl_2 \cdot 6H_2O$ | 20 mg/L |
| $NaMoO_4 \cdot 2H_2O$ | 40 mg/L |

Figure 1B:
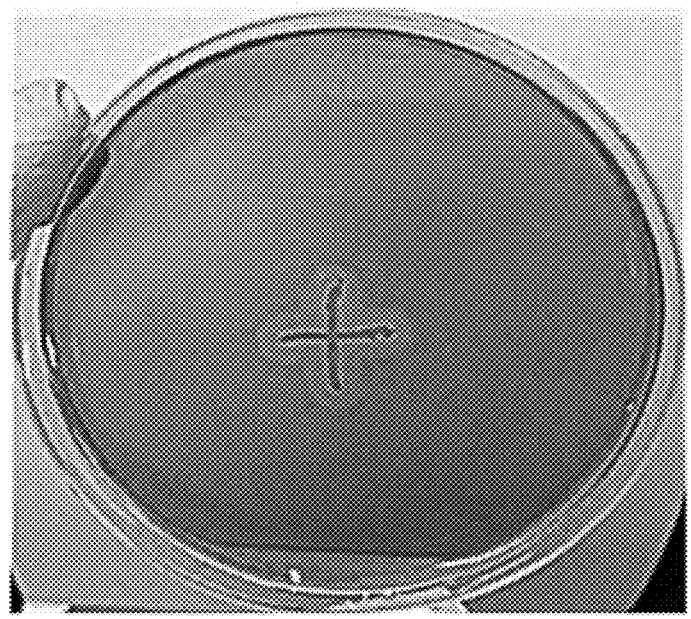

As seen from FIG. 1a and FIG. 1b, the strain harvested from Dongmak Beach showed the highest cellulose-degrading activity. FIG. 1a and FIG. 1b show the strain cultured in a cellulose-containing medium. FIG. 1b shows the result of staining the strain cultured as in FIG. 1a with Congo red. Staining with Congo red leads to red color as shown in FIG. 1b as the Congo red reagent is attached to cellulose. If the strain secretes cellulase, the cellulose around the strain in the medium is degraded and thus is not stained with Congo red, resulting in transparent color around the strain. The transparent cross-shaped portion in FIG. 1b reveals that the strain according to an exemplary embodiment of the present disclosure degrades cellulose.

Example 1-2

Phylogenic Analysis and Identification of Strain

Figure 2:
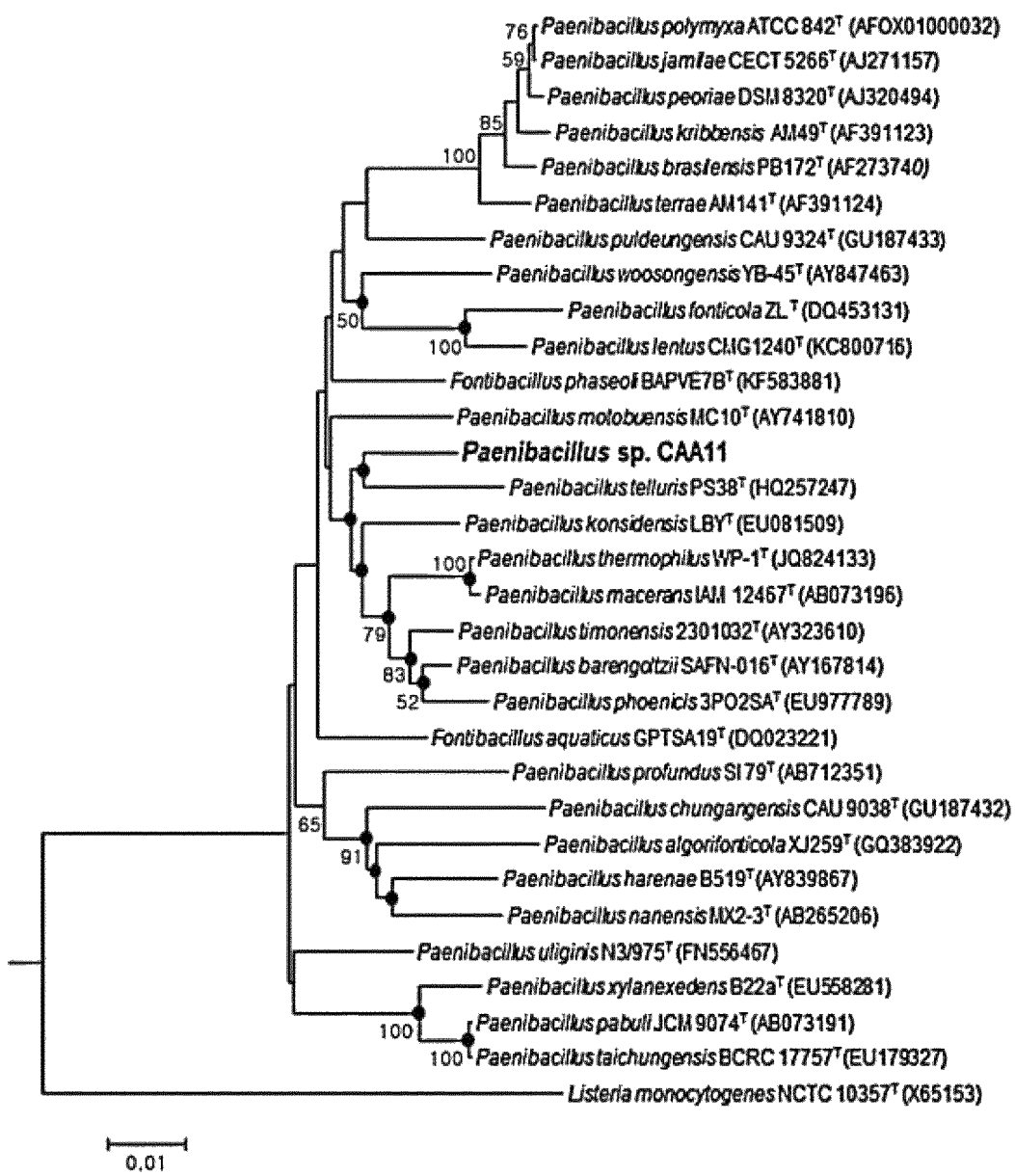
FIG. 2 shows the phylogenetic status of *Paenibacillus* sp. CAA11.

The genes of the strain harvested from Dongmak Beach, which showed the highest cellulase activity, were amplified by PCR. Primers used for the PCR amplification were 27F (5'-AGAGTTTGATCTGCTCAG-3', SEQ ID NO 1) and 1492R (5'-AAGGAGGTGATCCAGCCGCA-3', SEQ ID NO 2), and reaction conditions for the PCR were 94° C. for 5 minutes followed by 30 cycles of 94° C. for 1 minute, 55° C. for 1 minute and 72° C. for 1 minute and 30 seconds with a 10-minute incubation at 72° C. 16S rRNA nucleotide sequencing of the PCR products was conducted by Macrogen. A sequence of SEQ ID NO 3 was obtained and the strain was named as *Paenibacillus* sp. CAA11 after phylogenic analysis (FIG. 2).

```
SEQ ID NO 3:
    CTATACTGCAGTCGAGCGGAGTTATTTAGAAGCTTGCTTCTAAAT

AACTTAGCGGCGGACGGGTGAGTAACACGTAGGCAACCTGCCTGTAAGAC

TGGGATAACTACCGGAAACGGTAGCTAATACCGGATACACAAGTTCCTCG

CATGAGGGATTTGGGAAAGACGGAGCAATCTGTCACTTACGGATGGGCCT

GCGGCGCATTAGCTAGTTGGTGGGGTAACGGCTCACCAAGGCGACGATGC

GTAGCCGACCTGAGAGGGTGAACGGCCACACTGGGACTGAGACACGGCCC

AGACTCCTACGGGAGGCAGCAGTAGGGAATCTTCCGCAATGGACGAAAGT

CTGACGGAGCAACGCCGCGTGAGTGATGAAGGTTTTCGGATCGTAAAGCT

CTGTTGCCAGGGAAGAACGCTTGAGAGAGTAACTGCTCTTAAGGTGACGG
```

-continued

```
TACCTGAGAAGAAAGCCCCGGCTAACTACGTGCCAGCAGCCGCGGTAATA
CGTAGGGGGCAAGCGTTGTCCGGAATTATTGGGCGTAAAGCGCGCGCAGG
CGGCCATTTAAGTCTGGTGTTTAATCCTGGAGCTCAACTCCGGGTCGCAC
TGGAAACTGGGTGGCTTGAGTGCAGAAGAGGAGAGTGGAATTCCACGTGT
AGCGGTGAAATGCGTAGAGATGTGGAGGAACACCAGTGGCGAAGGCGACT
CTCTGGGCTGTAACTGACGCTGAGGCGCGAAAGCGTGGGGAGCAAACAGG
ATTAGATACCCTGGTAGTCCACGCCGTAAACGATGAATGCTAGGTGTTAG
GGGTTTCGATACCCTTGGTGCCGAAGTTAACACATTAAGCATTCCGCCTG
GGGAGTACGGTCGCAAGACTGAAACTCAAAGGAATTGACGGGGACCCGCA
CAAGCAGTGGAGTATTGTGGTTTAATTCGAAGCAACGCGAAGAACCTTAC
CAGGTCTTGACATCCCTCTGACCGGTACAGAGATGTACCTTTCCTTTACG
GACAAAGGAAACAGGTGGGTGCATGGTTGTCGTCAGCTCGTGTCGTGAGA
TGTTGGGTTAAGTCCCGCAACGAGCGCAACCCTTAACTTTAGTTGCCAGC
AGGTCAAGCTGGGCACTCTAGAGTGACTGCCGGTGACAAACCGGAGGAAG
GTGGGGATGACGTCAAATCATCATGCCCCTTATGACCTGGGCTACACACG
TACTACAATGGCCGGTACAACGGGAAGCGAAGGAGCGATCTGGAGCGAAT
CCTAGAAAAGCCGGTCTCAGTTCGGATTGCAGGCTGCAACTCGCCTGCAT
GAAGTCGGAATTGCTAGTAATCGCGGATCAGCATGCCGCGGTGAATACGT
TCCCGGGTCTTGTACACACCGCCCGTCACACCACGAGAGTTTACAACACC
CGAAGTCGGTGAGGTAACCCGCAAGGGGCCAGCCGCCGAAG
```

Test Example 1

Determination of Culturing Condition Optimized for *Paenibacillus* sp. CAA11

Test Example 1-1

Determination of Medium Composition

The growth of *Paenibacillus* sp. CAA11 in M9 medium which is commonly used in the culturing of *Bacillus* was measured with time.

The composition of the M9 medium used to culture *Paenibacillus* is described in Table 3. The composition of the trace elements in Table 3 was the same as in Table 2 with FeSO$_4$ further added. The strain was cultured for 24 hours at 37° C. while agitating at 200 rpm and adding 5 g/L glucose. The growth of the strain was investigated by measuring absorbance (OD$_{600}$). Specifically, the absorbance was measured at 600 nm using a spectrophotometer after diluting part of the culture with distilled water.

TABLE 3

| Medium composition | |
|---|---|
| Na$_2$HPO$_4$•7H$_2$O | 12.8 g/L |
| KH$_2$PO$_4$ | 3 g/L |
| NaCl | 0.5 g/L |
| NH$_4$Cl | 1 g/L |
| MgSO$_4$•7H$_2$O | 0.492 g/L |
| CaCl$_2$ | 0.111 g/L |
| Trace elements | 1 mL |
| pH | 7 |

Figure 3:
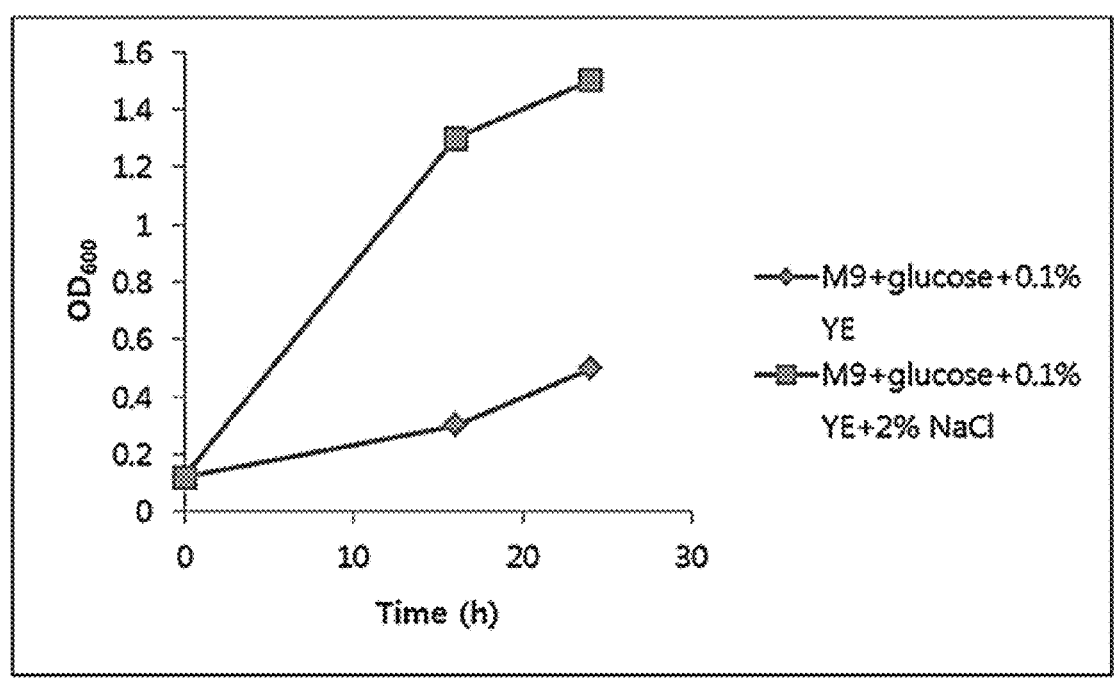
FIG. 3, FIGS. 4*a*-4*c* and FIGS. 5*a*-5*c* show the growth of *Paenibacillus* sp. CAA11 under different culturing conditions.

As seen from FIG. 3, the growth of *Paenibacillus* sp. CAA11 was significantly increased as compared to the M9 medium supplemented with 5 g/L glucose and 0.1% yeast extract when 2% (wt/v) NaCl was further added.

Test Example 1-2

Determination of pH Condition for Strain Culturing

Experiment was conducted as follows to compare the growth of *Paenibacillus* sp. CAA11 depending on pH conditions.

First, *Paenibacillus* sp. CAA11 was cultured overnight in the M9 medium with the composition of Table 3. Then, after adding 5 g/L glucose, a seed culture of the cultured *Paenibacillus* sp. CAA11 was subcultured in M9 medium adjusted to pH 5, 6 or 7 at 37° C. while agitating at 200 rpm. Growth curves as shown in FIGS. 4a-4c were obtained by measuring absorbance (OD$_{600}$) using an absorption spectrophotometer (Cary 60 UV-Vis, Agilent Technologies, USA) with 10-minute intervals.

Figure 4A:
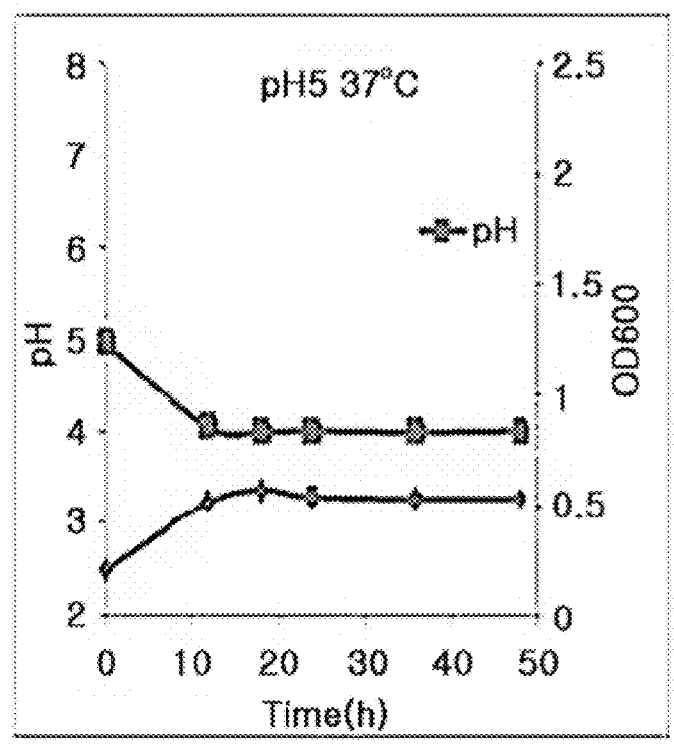
Figure 4B:
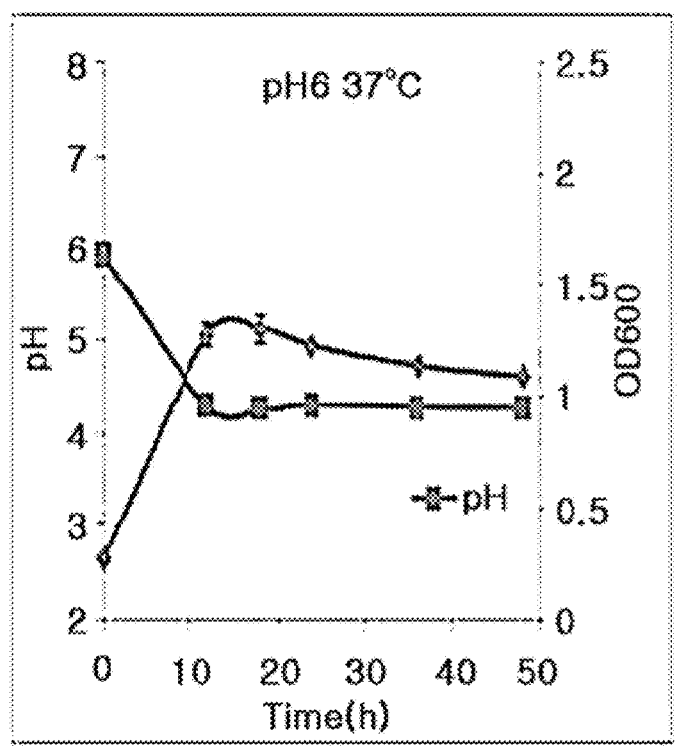
Figure 4C:
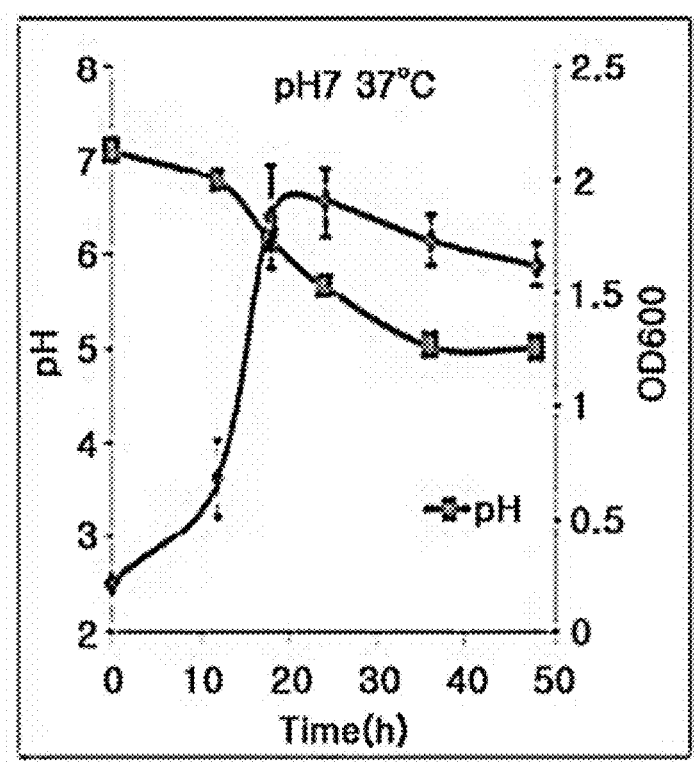

From FIGS. 4a-4c, it can be seen that the growth of the strain increased at pH 6 and pH 7. In particular, the strain showed explosive growth at pH 7.

Test Example 1-3

Determination of Temperature Condition for Strain Culturing

Experiment was conducted as follows to compare the growth of *Paenibacillus* sp. CAA11 depending on temperature conditions.

First, *Paenibacillus* sp. CAA11 was cultured overnight in the M9 medium with the composition of Table 3. Then, after adjusting to pH 7 and adding 5 g/L glucose, a seed culture of the cultured *Paenibacillus* sp. CAA11 was subcultured in M9 medium at 30° C., 37° C. or 50° C. while agitating at 200 rpm. Growth curves as shown in FIGS. 5a-5c were obtained by measuring absorbance (OD$_{600}$) using an absorption spectrophotometer (Cary 60 UV-Vis, Agilent Technologies, USA).

Figure 5A:
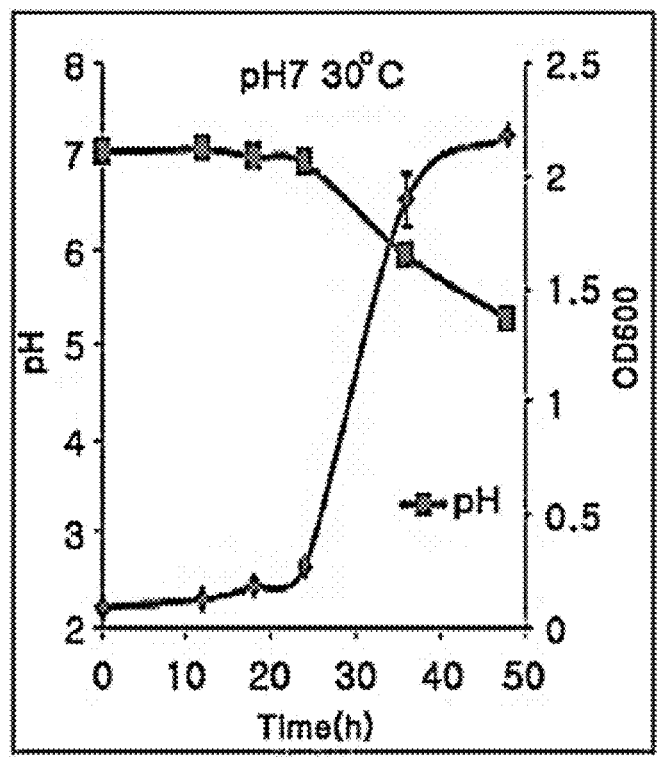
Figure 5B:
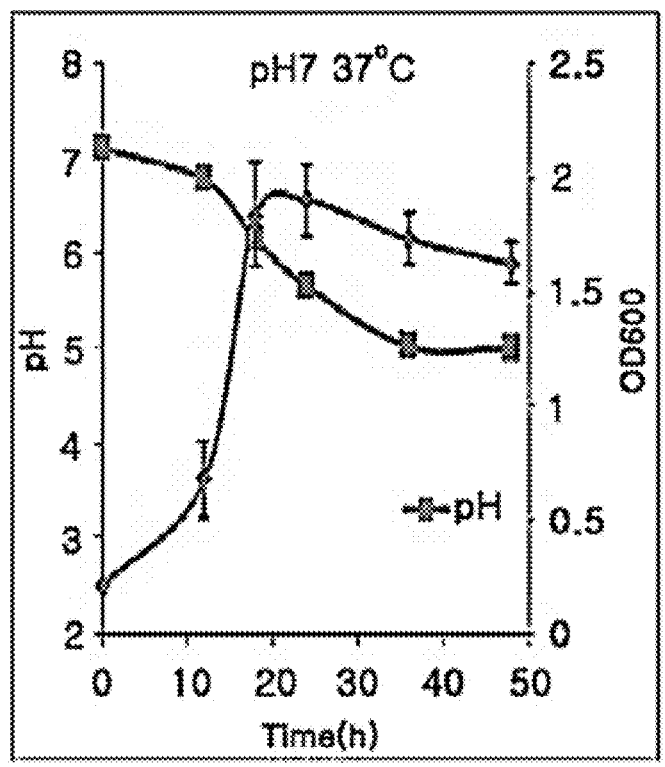
Figure 5C:
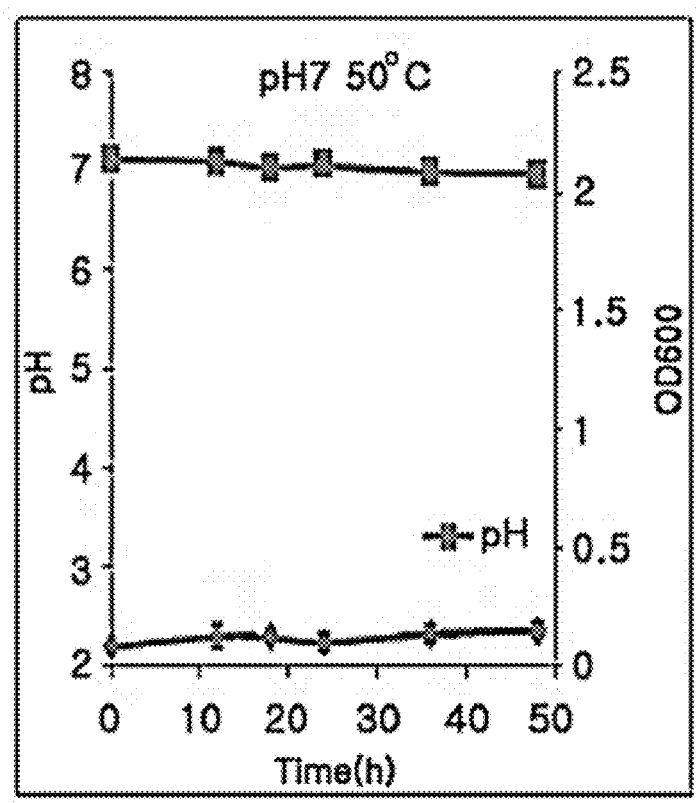

From FIGS. 5a-5c, it can be seen that the strain showed explosive growth at 30° C. and 37° C. as compared to at 50° C.

Test Example 2-1

Saccharification and Fermentation Capabilities of *Paenibacillus* sp. CAA11

Experiment was conducted as follows to investigate whether *Paenibacillus* sp. CAA11 can use sugars other than glucose.

First, *Paenibacillus* sp. CAA11 was cultured overnight at 37° C. in the M9 medium with the composition of Table 3 supplemented with 0.1% yeast extract, 2% NaCl and 5 g/L glucose while agitating at 200 rpm. The seed culture was subcultured in M9 medium supplemented with 0.1% yeast extract, 2% NaCl and glucose, xylose or cellobiose as a carbon source after diluting to 1/100. While agitating at 37°

C. at 200 rpm, 1 mL of each culture was sampled. The sample was diluted 10 times and the quantity of acetic acid as a fermentation product of glucose, xylose or cellobiose was analyzed by HPLC (Agilent 1260 (Waldbronn, Germany), refractive index detector (RID); Aminex HPX-87 H ion exclusion column (300 mm×7.8 mm, Bio-Rad, Hercules, Calif., USA)).

Figure 6A:
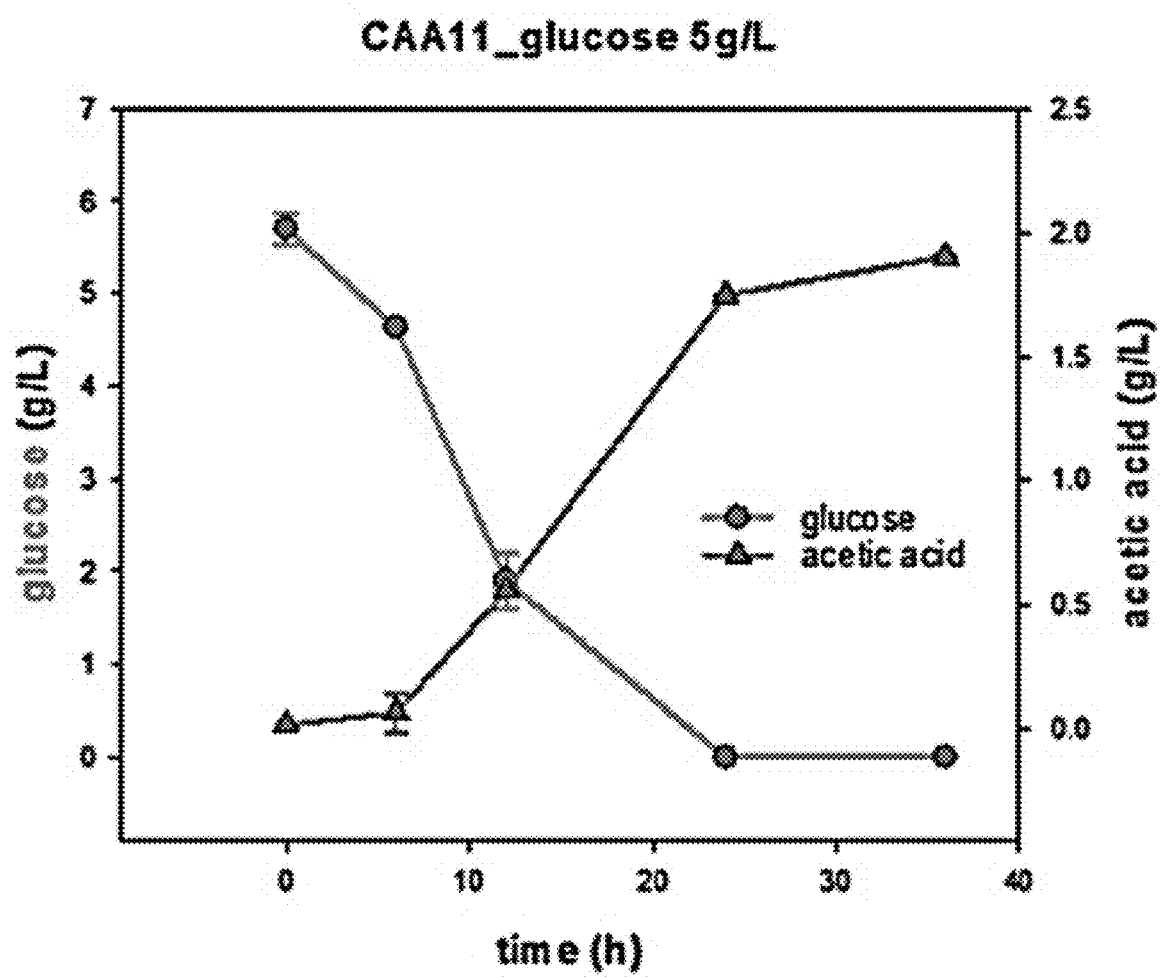
FIGS. 6*a*-6*c* show the consumption of sugars and the production amount of products when *Paenibacillus* sp. CAA11 is cultured with a disaccharide or a monosaccharide.
Figure 6B:
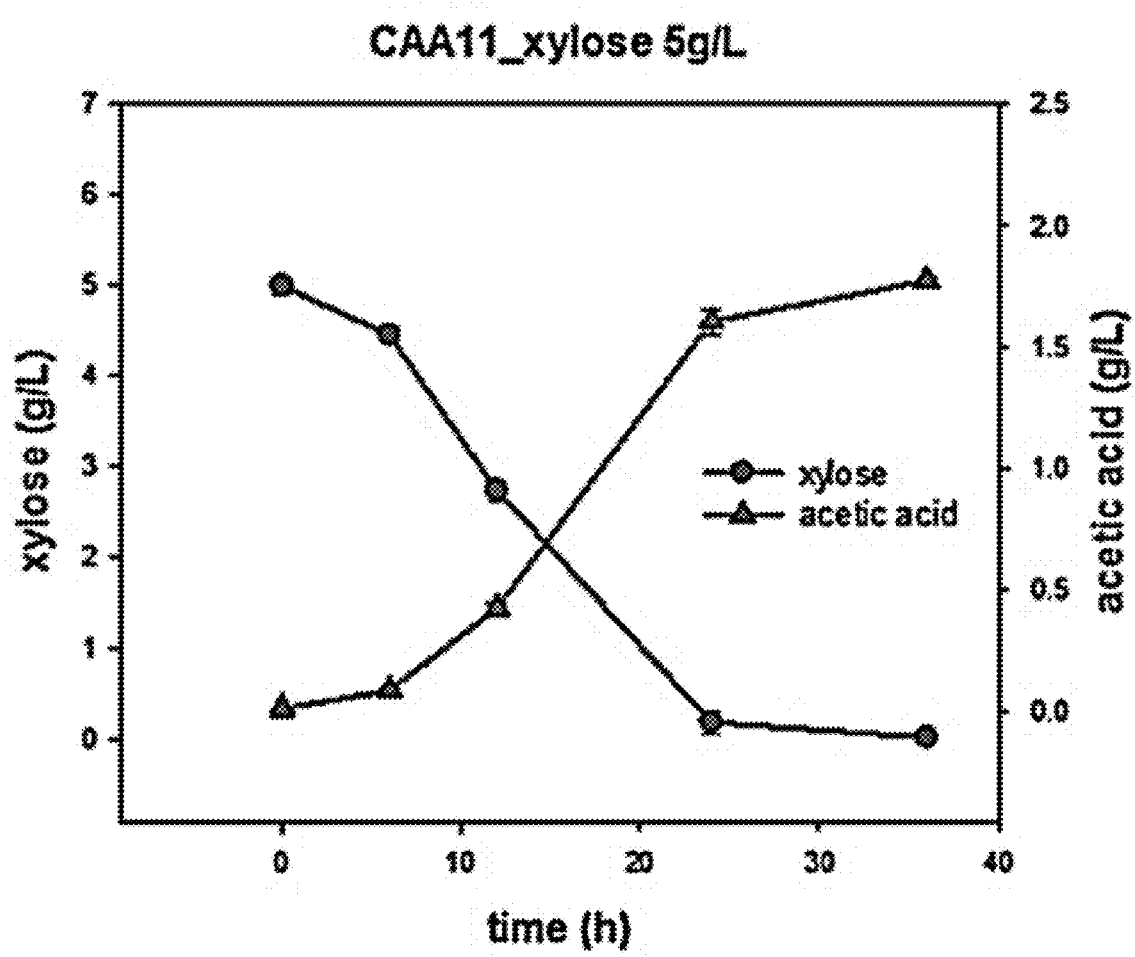
Figure 6C:
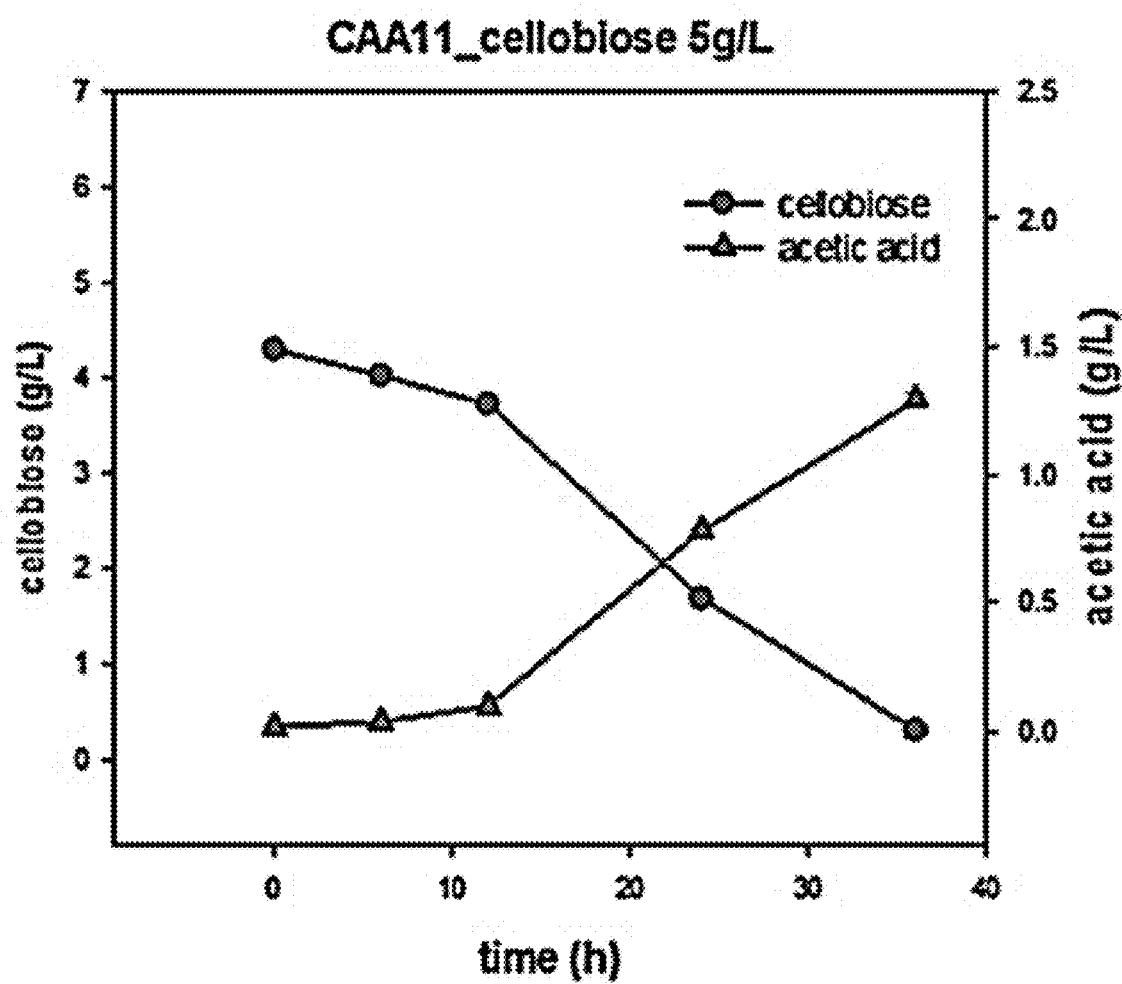

From FIGS. 6a-6c, it can be seen that the *Paenibacillus* sp. CAA11 of the present disclosure can produce acetic acid which can be used as a bioenergy source material through fermentation using a monosaccharide such as the hexose glucose and the pentose xylose as a carbon source. In addition, it can be seen that the *Paenibacillus* sp. CAA11 of the present disclosure can produce acetic acid when the disaccharide cellobiose is used as a carbon source. Accordingly, it can be seen that the *Paenibacillus* sp. CAA11 of the present disclosure can use various sugars produced during the saccharification of biomass as carbon sources and can produce bioenergy source materials through fermentation.

Test Example 2-2

Saccharification and Fermentation Capabilities of *Paenibacillus* sp. CAA11 in the Presence of Two or More Carbon Sources Experiment was conducted to investigate whether *Paenibacillus* sp. CAA11 has saccharification and fermentation capabilities for two or more carbon sources under the same condition as in Test Example 2-1. Specifically, glucose and cellobiose or cellobiose and xylose were used as carbon sources. The other conditions were the same as in Test Example 2-1.

Figure 7A:
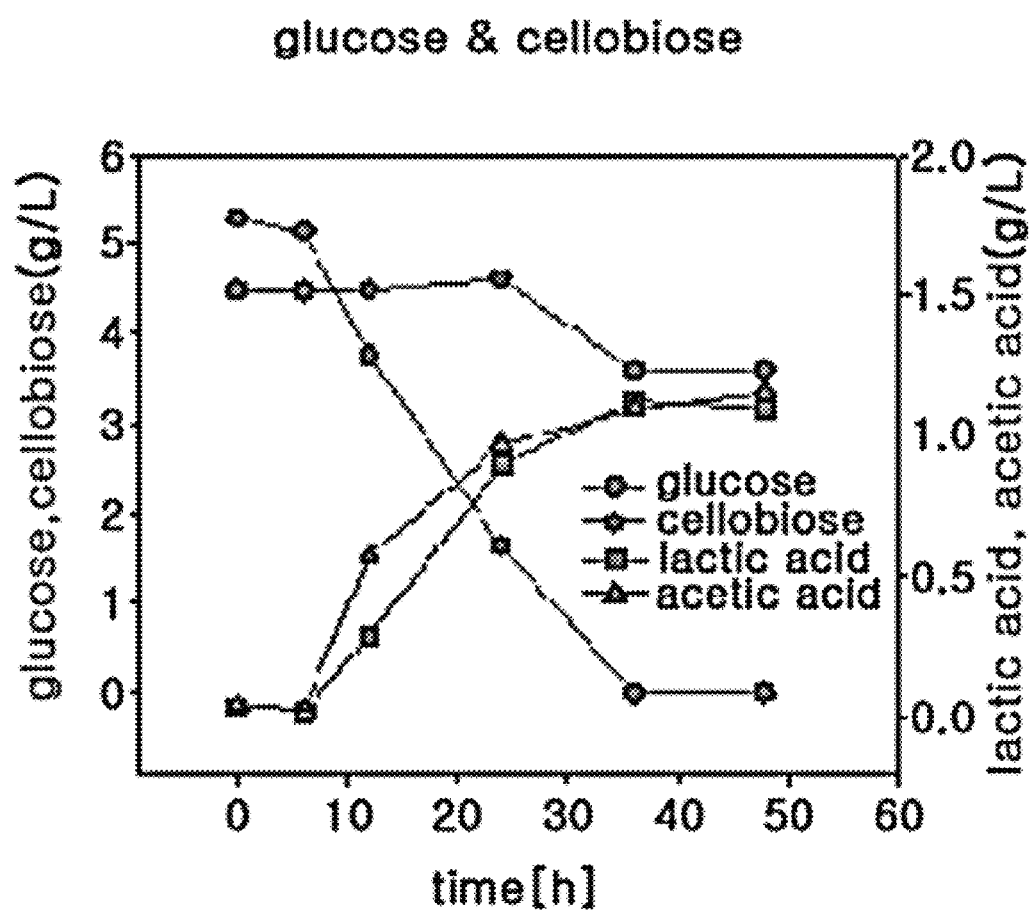
FIG. 7*a* and FIG. 7*b* show a result of analyzing the consumption of sugars and the production of fermentation products when *Paenibacillus* sp. CAA11 is cultured with the hexose glucose and the disaccharide cellobiose or with the pentose xylose and the disaccharide cellobiose at the same time.
Figure 7B:
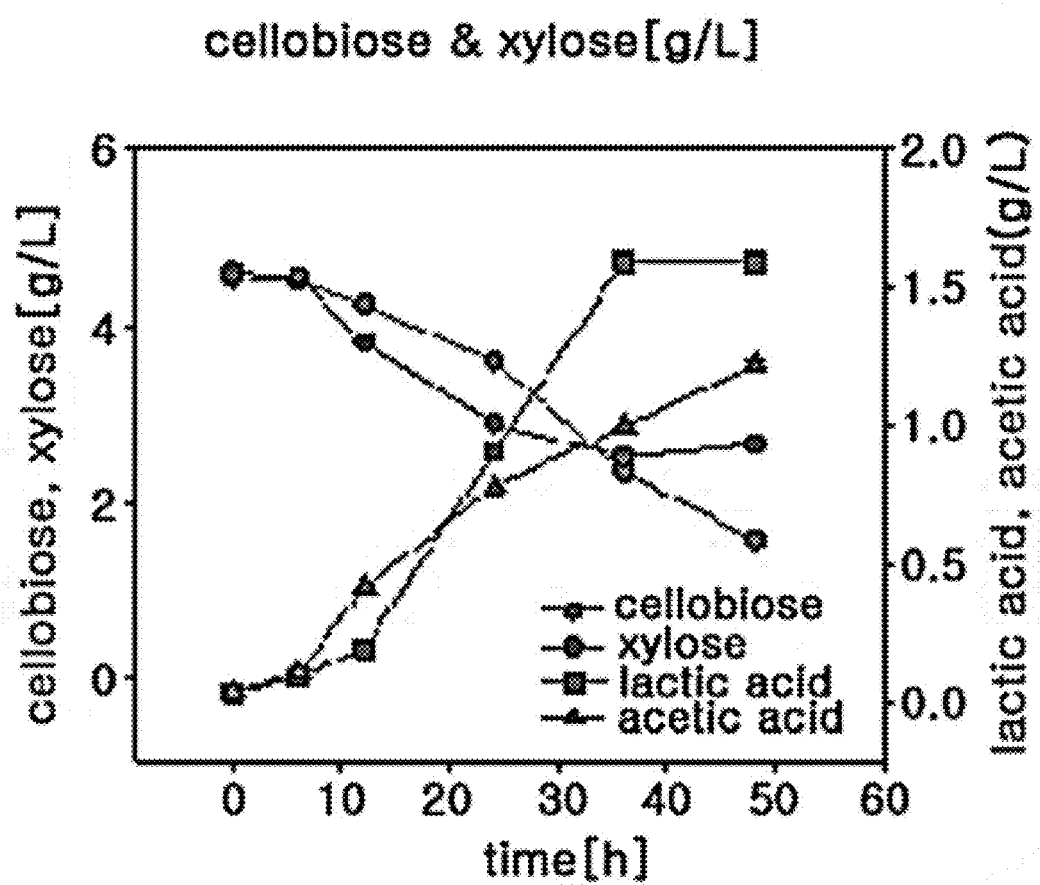

From FIG. 7a and FIG. 7b, it can be seen that the *Paenibacillus* sp. CAA11 of the present disclosure can produce acetic acid and lactic acid at the same time using the monosaccharide hexose glucose and the disaccharide cellobiose as carbon sources. In addition, it can be seen from FIG. 7a and FIG. 7b that the *Paenibacillus* sp. CAA11 of the present disclosure can produce acetic acid and lactic acid at the same time using the monosaccharide pentose xylose and the disaccharide cellobiose as carbon sources. Because the *Paenibacillus* sp. CAA11 of the present disclosure can use glucose, which is the major reducing sugar of cellulose, and cellobiose, which is the major reducing sugar of hemicellulose, as carbon sources at the same time, it allows for effective saccharification and fermentation of cellulose and hemicellulose obtained after pretreatment of biomass, specifically lignocellulosic biomass.

Test Example 3

Saccharification and Fermentation Capabilities of *Paenibacillus sp. CAA*11 Depending on Cellulose Solubility 10 g of crystalline cellulose Avicel PH-101 was mixed with 100 mL of 85% phosphoric acid and treated at 50° C. for 6 hours. After washing 4 times with sterilized distilled water, 30 mL of 2N NaOH was added and the mixture was allowed to stand overnight at 4° C., followed by washing with sterilized distilled water until pH reached about 7.0. The pretreated RAC (regenerated amorphous cellulose) was used as insoluble cellulose and CMC (carboxymethyl cellulose) was used as soluble cellulose.

A seed culture cultured overnight in M9 medium supplemented with 0.1% (wt/v) yeast extract, 2% (wt/v) NaCl and 5 g/L glucose was cultured in M9 medium with the composition of Table 3 supplemented with 0.1% (wt/v) yeast extract, 2% (wt/v) NaCl and 5 g/L CMC (carboxymethyl cellulose) as soluble cellulose or in M9 medium supplemented with 0.1% (wt/v) yeast extract, 2% (wt/v) NaCl and 5 g/L RAC (regenerated amorphous cellulose) as insoluble cellulose. As a control group, the strain was cultured in the same medium lacking cellulose. The strain was cultured at 37° C. for 42 hours while agitating at 200 rpm. The growth of *Paenibacillus* sp. CAA11 was measured by sampling 1 mL of the culture at different times.

Figure 8:
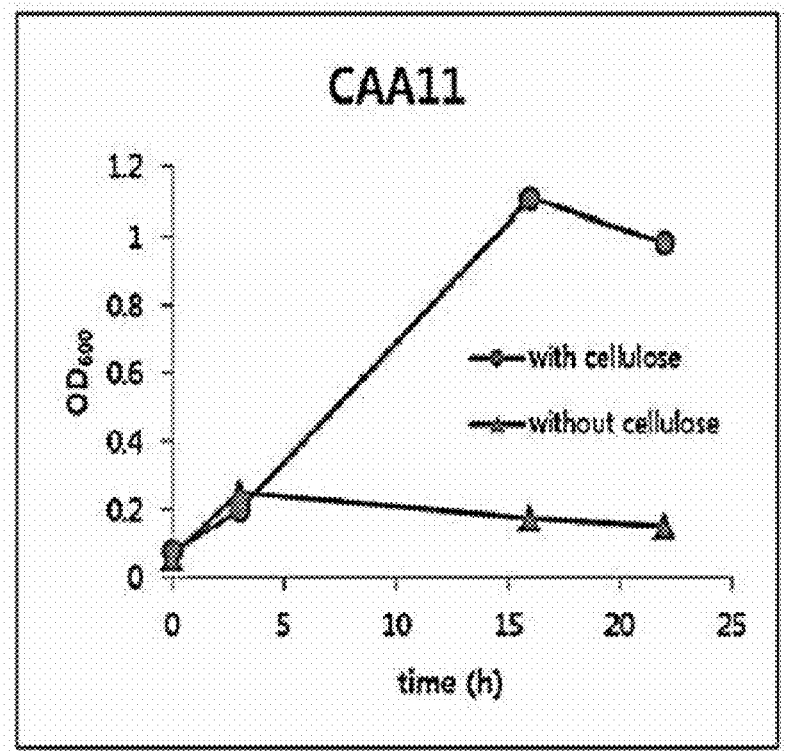
FIG. 8 shows a result of measuring the growth of *Paenibacillus* sp. CAA11 in a medium to which a soluble cellulose that dissolves well in a liquid has been added.
Figure 9:
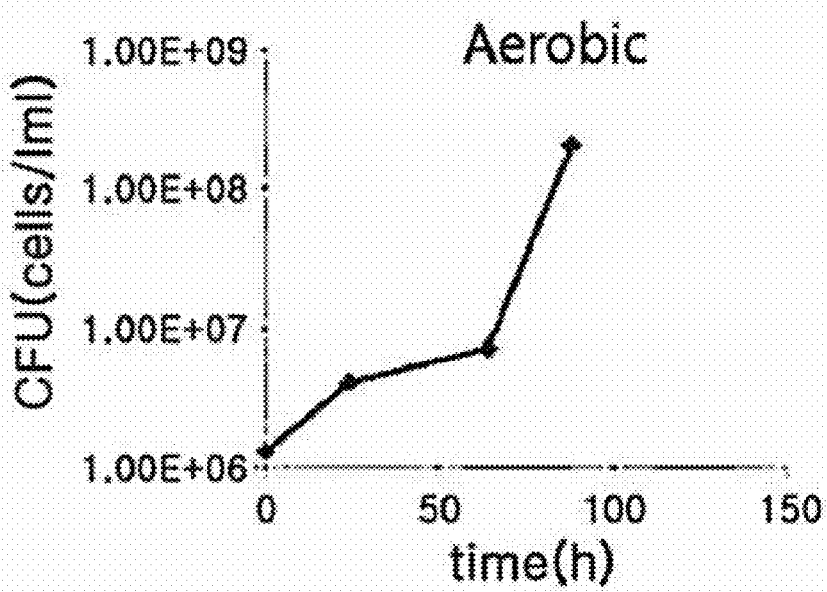
FIG. 9 shows a result of measuring the growth of *Paenibacillus* sp. CAA11 in a medium to which an insoluble cellulose has been added.
Figure 10A:
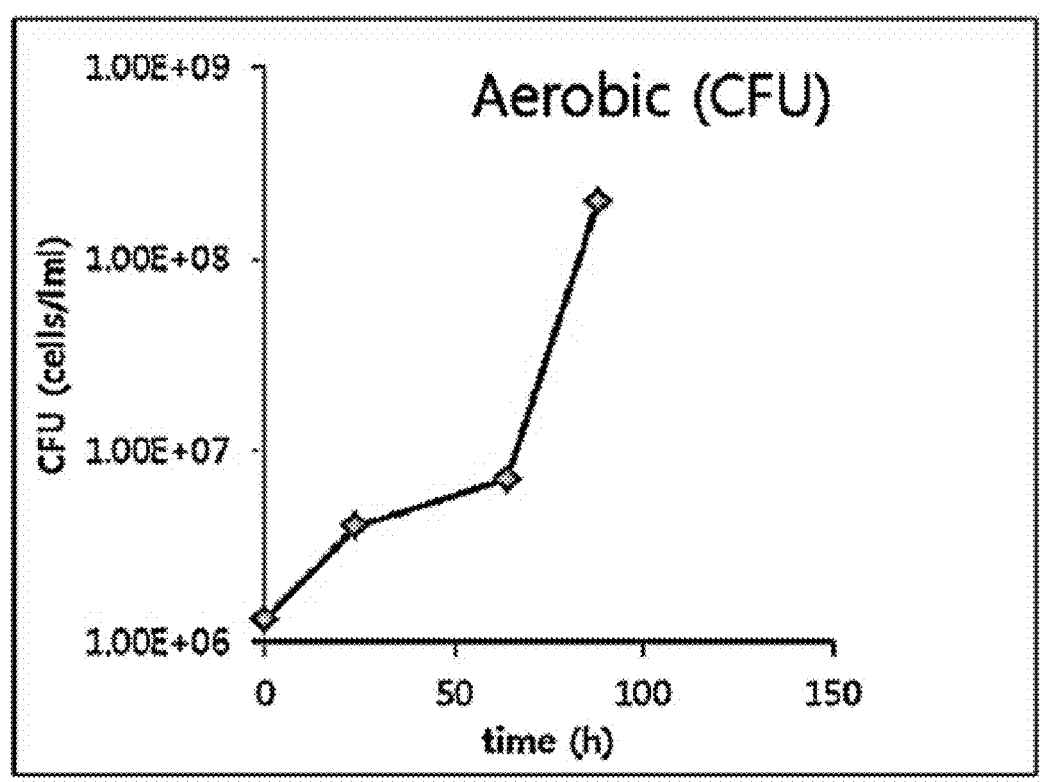
FIGS. 10a-10d show a result of culturing *Paenibacillus* sp. CAA11 in an insoluble cellulose medium in aerobic condition and anaerobic condition. It can be seen that the growth of the strain has increased (FIG. 10a and FIG. 10b) and bioenergy source materials have been produced (FIG. 10c and FIG. 10d).
Figure 10B:
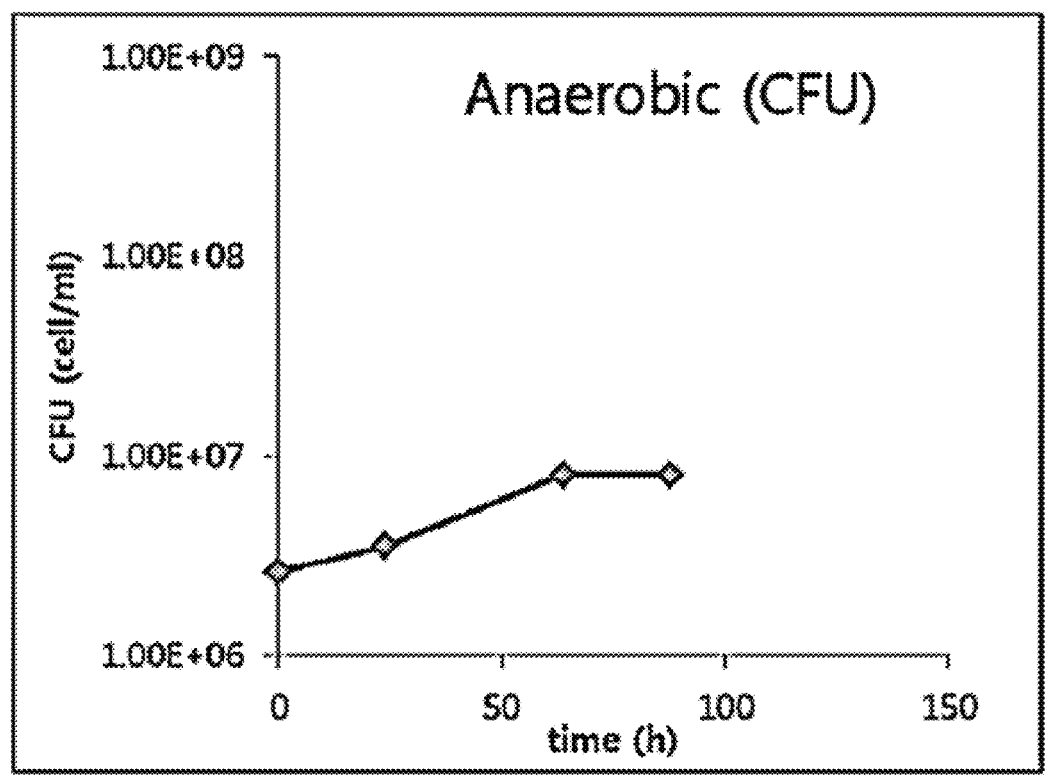
Figure 10C:
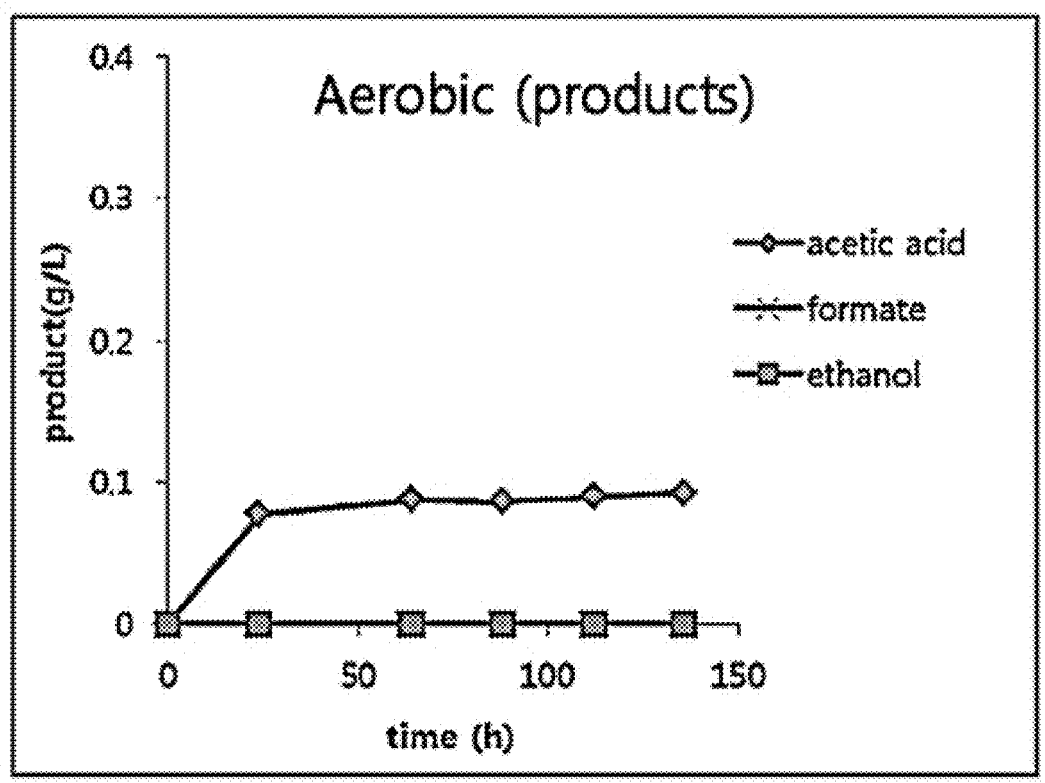
Figure 10D:
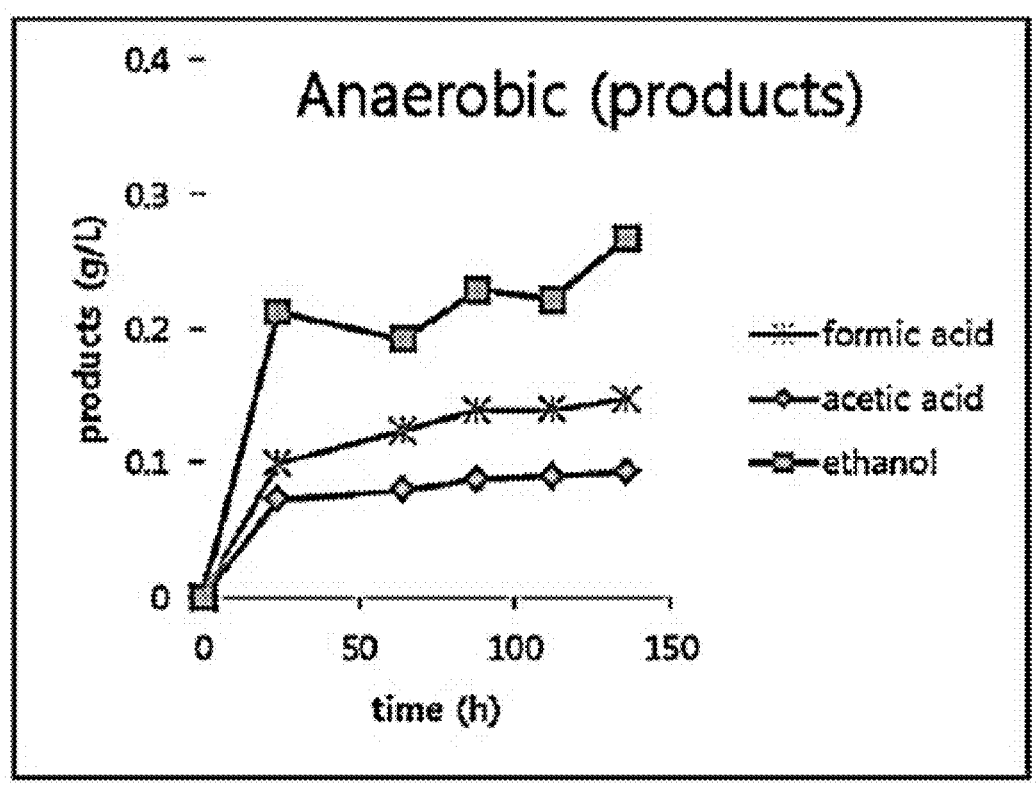

For the strain cultured in the medium containing the soluble cellulose CMC, absorbance ($OD_{600}$) was measured using an absorption spectrophotometer (Cary 60 UV-Vis, Agilent Technologies, USA). The result is shown in FIG. 8. For the strain cultured in the medium containing the insoluble cellulose RAC, the growth of the strain cannot be measured with absorbance because the cellulose remains opaque in the medium. Therefore, the growth of the strain was investigated by measuring the colony forming unit (CFU) at different times. The colony forming unit (CFU) was determined by plating the sampled culture on a solid medium after diluting to $1/10^3$-$10^8$ and counting the number of colonies per 1 mL of the culture. The result is shown in FIG. 9. From FIG. 8 and FIG. 9, it can be seen that *Paenibacillus* sp. CAA11 can grow regardless of the solubility of cellulose in liquid. Accordingly, it can be seen that the strain can maintain superior saccharification and fermentation capabilities without being affected by the type of cellulose.

Test Example 4

Saccharification and Fermentation Capabilities of *Paenibacillus* sp. CAA11 in Anaerobic and Aerobic Conditions A seed culture cultured overnight in M9 medium with the composition of Table 3 supplemented with 0.1% (wt/v) yeast extract, 2% (wt/v) NaCl and 5 g/glucose was cultured in aerobic or anaerobic condition in M9 medium supplemented with 0.1% (wt/v) yeast extract, 2% (wt/v) NaCl and 5 g/L RAC (regenerated amorphous cellulose) as insoluble cellulose.

For the aerobic condition, the strain was cultured in 20 mL of the medium in a 100-mL flask at 37° C. while agitating at 200 rpm. For the anaerobic condition, the strain was precultured in the medium in a serum bottle after purging with argon and then cultured under the same condition as the aerobic condition (37° C., 200 rpm). The growth of the strain was determined by sampling 1 mL of the culture at different times and measuring the colony forming unit (CFU). Products were measured by HPLC after diluting to 1/10. The colony forming unit (CFU) was used to determine the growth of the strain because it cannot be measured with absorbance since the insoluble cellulose RAC remains opaque in the medium.

The CFU was determined by plating the sampled culture on a solid medium after diluting to $1/10^3$-$10^8$ and counting the number of colonies per 1 mL of the culture. The products acetic acid, formic acid and ethanol were analyzed by HPLC (Agilent 1260 (Waldbronn, Germany), refractive index detector (RID); Aminex HPX-87 H ion exclusion column (300 mm×7.8 mm, Bio-Rad, Hercules, Calif., USA). The result is shown in FIGS. 10a-10d.

From FIGS. 10a-10d, it can be seen that *Paenibacillus* sp. CAA11 can grow well both in aerobic and anaerobic conditions and can produce fermentation products both in aerobic and anaerobic conditions.

Example 3

Screening of Promoter for Use in Transformation for Overexpressing Protein in *Paenibacillus* sp. CAA11

Establishment of method for transforming *Paenibacillus* sp. CAA11 Because no transformation method is established for *Paenibacillus*, various vectors including a cloning vector for use in *Bacillus*, a vector for genomic insertion and a vector for labeling a target genome were acquired from the *Bacillus* Genetic Stock Center (BGSC, USA).

A method for introducing DNA into CAA11 was established by trying various transformation techniques for DNA insertion under various conditions. Because *Paenibacillus* sp. CAA11 is a Gram-positive bacterium having a thick cell wall, 0.5 M sorbitol was added when preparing the cells to be transformed to raise osmotic pressure in order to increase the efficiency of DNA introduction. After conducting transformation using plasmids of various sizes, it was confirmed that the plasmids were successfully introduced into CAA11 as shown in Table 4.

TABLE 4

| Plasmids | pNW33N | pAD123 | pHCMC02 | pAD43-25 | pHCMC05 | Negative |
|---|---|---|---|---|---|---|
| Size (bp) | 4217 | 5952 | 6866 | 7262 | 8321 | |
| Colony | 105 | 80 | 37 | 13 | 0 | 0 |

Preparation of Vector for Measurement of Promoter Intensity

Figure 11A:
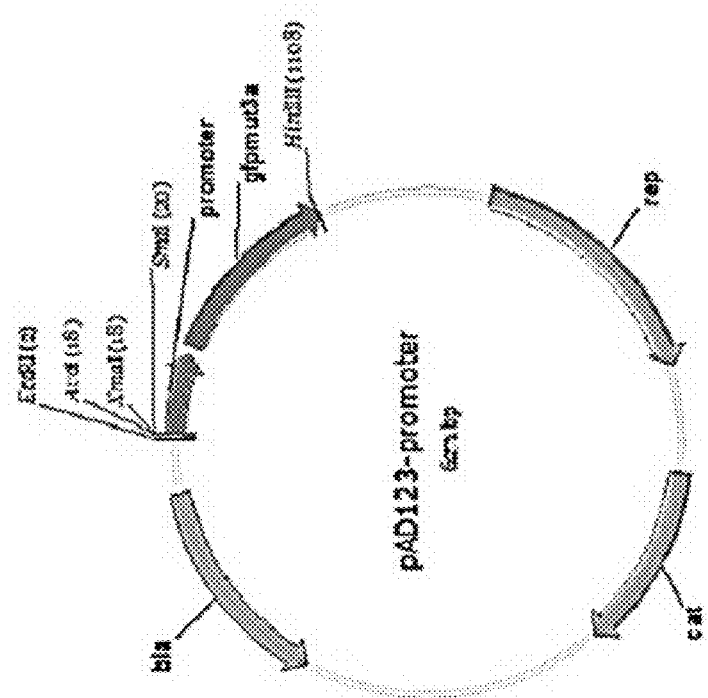
FIG. 11a and FIG. 11b respectively show the schematic structure of a vector (pAD123-promoter-GFP) for measuring promoter intensity (FIG. 11a) and a result of measuring promoter intensity (FIG. 11b) according to an exemplary embodiment of the present disclosure.
Figure 11A:
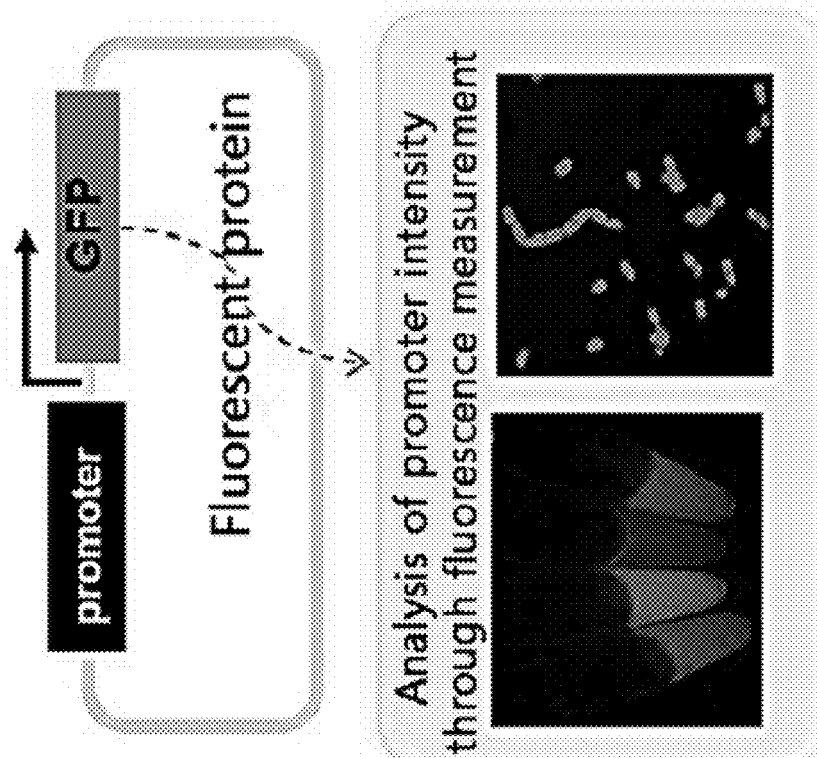

Vectors for measuring promoter intensity were prepared by inserting 8 combinations of promoters into the pAD123 vector which contains the fluorescent protein GFP gene. The used promoters are shown in Table 5. A schematic of a pAD123-promoter vector is shown in FIG. 11a.

PCR was conducted by one cycle of predenaturation at 98° C. for 2 minutes followed by 30 cycles of denaturation at 98° C. for 10 seconds, annealing at 60° C. for 10 seconds and elongation at 72° C. for 10 seconds. Then, one cycle of extra elongation was conducted at 72° C. for 5 minutes.

Then, after cleaving pAD123 and promoter PCR products with SmaI and BamHI restriction enzymes present at the MCS sites of the pAD123 plasmid, the promoter PCR products were ligated with pAD123.

Finally, pAD123-promoter was transformed into *E. coli* DH5a and plated onto an LB agar plate containing 25 µg/mL Cm. Then, the recombinant plasmid was identified by colony inoculation.

TABLE 5

Promoters used in promoter intensity measurement

| Number of used promoters | Used promoters | Sequence |
|---|---|---|
| 1 | Pspac (SEQ ID NO 7) | aggccttacacagcccagtccagactattcggcactgaaattatgggtgaagtggtc aagacctcactaggcaccttaaaaatagcgcaccctgaagaagatttatttgaggta gcccttgcctacctagcttccaagaaagatatcctaacagcacaagagcggaaag atgttttgttctacatccagaacaacctctgctaaaattcctgaaaaattttgcaaaaag ttgttgactttatctacaaggtgtggcataatgtgtggaattgtgagcggataacaatta agcttaaggaggtga |
| | PHpall (SEQ ID NO 8) | gatcttctcaaaaaatactacctgtcccttgctgattttaaacgagcacgagagcaaa accccctttgctgaggtggcagagggcaggttttttttgtttcttttttctcgtaaaaaaaa gaaaggtcttaaaggttttatggttttggtcggcactgccgacagcctcgcagagcac acactttatgaatataaagtatagtgtgttatactttacttggaagtggttgccggaaag agcgaaaatgcctcacatttgtgccacctaaaaaggagcgatttacat |
| | P43 (SEQ ID NO 9) | tgataggtggtatgttttcgcttgaacttttaaatacagccattgaacatacggttgattta ataactgacaaacatcaccctcttgctaaagcggccaaggacgctgccgccgggg ctgtttgcgttttttgccgtgatttcgtgtatcattggtttacttatttttttgccaaagctgtaatg gctgaaaattcttacattttattttacattttttagaaatgggcgtgaaaaaaagcgcgcg attatgtaaaatataaagtgatagc |
| 2 | Pspac P43 (SEQ ID NO 10) | aggccttacacagcccagtccagactattcggcactgaaattatgggtgaagtggtc aagacctcactaggcaccttaaaaatagcgcaccctgaagaagatttatttgaggta gcccttgcctacctagcttccaagaaagatatcctaacagcacaagagcggaaag atgttttgttctacatccagaacaacctctgctaaaattcctgaaaaattttgcaaaaag ttgttgactttatctacaaggtgtggcataatgtgtggaattgtgagcggataacaatta agcttaaggaggtgaggatcctgataggtggtatgttttcgcttgaacttttaaatacag |

TABLE 5-continued

Promoters used in promoter intensity measurement

| Number of used promoters | Used promoters | Sequence |
|---|---|---|
| | | ccattgaacatacggttgatttaataactgacaaacatcaccctcttgctaaagcggc<br>caaggacgctgccgccgggctgtttgcgttttgccgtgatttcgtgtatcattggttta<br>cttattttttgccaaagctgtaatggctgaaaattcttacatttattttacattttagaaatg<br>ggcgtgaaaaaagcgcgcgattatgtaaaatataaagtgatagc |
| | PHpall<br>(SEQ ID<br>NO 11) | P43gatcttctcaaaaaatactacctgtcccttgctgattttttaaacgagcacgagagcaa<br>aaccccccttttgctgaggtggcagagggcaggttttttttgtttcttttttctcgtaaaaaaa<br>agaaaggtcttaaaggttttatggttttggtcggcactgccgacagcctcgcagagca<br>cacactttatgaatatataaagtatagtgtgttatactttacttggaagtggttgccggaaa<br>gagcgaaaatgcctcacatttgtgccacctaaaaaggagcgatttacatggatcctg<br>ataggtggtatgttttcgcttgaactttaaatacagccattgaacatacggttgatttaat<br>aactgacaaacatcaccctcttgctaaagcggccaaggacgctgccgccgggct<br>gtttgcgttttgccgtgatttcgtgtatcattggtttactttattttttttgccaaagctgtaatgg<br>ctgaaaattcttacatttatttttacattttagaaatgggcgtgaaaaaaagcgcgcgat<br>tatgtaaaatataaagtgatagc |
| | P43<br>(SEQ ID<br>NO 5) | P43 tgataggtggtatgttttcgcttgaactttaaatacagccattgaacatacggttgattta<br>ataactgacaaacatcaccctcttgctaaagcggccaaggacgctgccgccgggg<br>ctgtttgcgttttgccgtgatttcgtgtatcattggtttactttattttttttgccaaagctgtaatg<br>gctgaaaattcttacatttatttttacattttagaaatgggcgtgaaaaaagcgcgcg<br>attatgtaaaatataaagtgatagcggatcctgataggtggtatgttttcgcttgaactttt<br>aaatacagccattgaacatacggttgatttaataactgacaaacatcaccctcttgct<br>aaagcggccaaggacgctgccgccgggctgtttgcgttttgccgtgatttcgtgtat<br>cattggtttacttattttttttgccaaagctgtaatggctgaaaattcttacatttattttacattt<br>ttagaaatgggcgtgaaaaaaagcgcgcgattatgtaaaatataaagtgatagc |

Preparation of Cellulase Expression Vector

Figure 12:
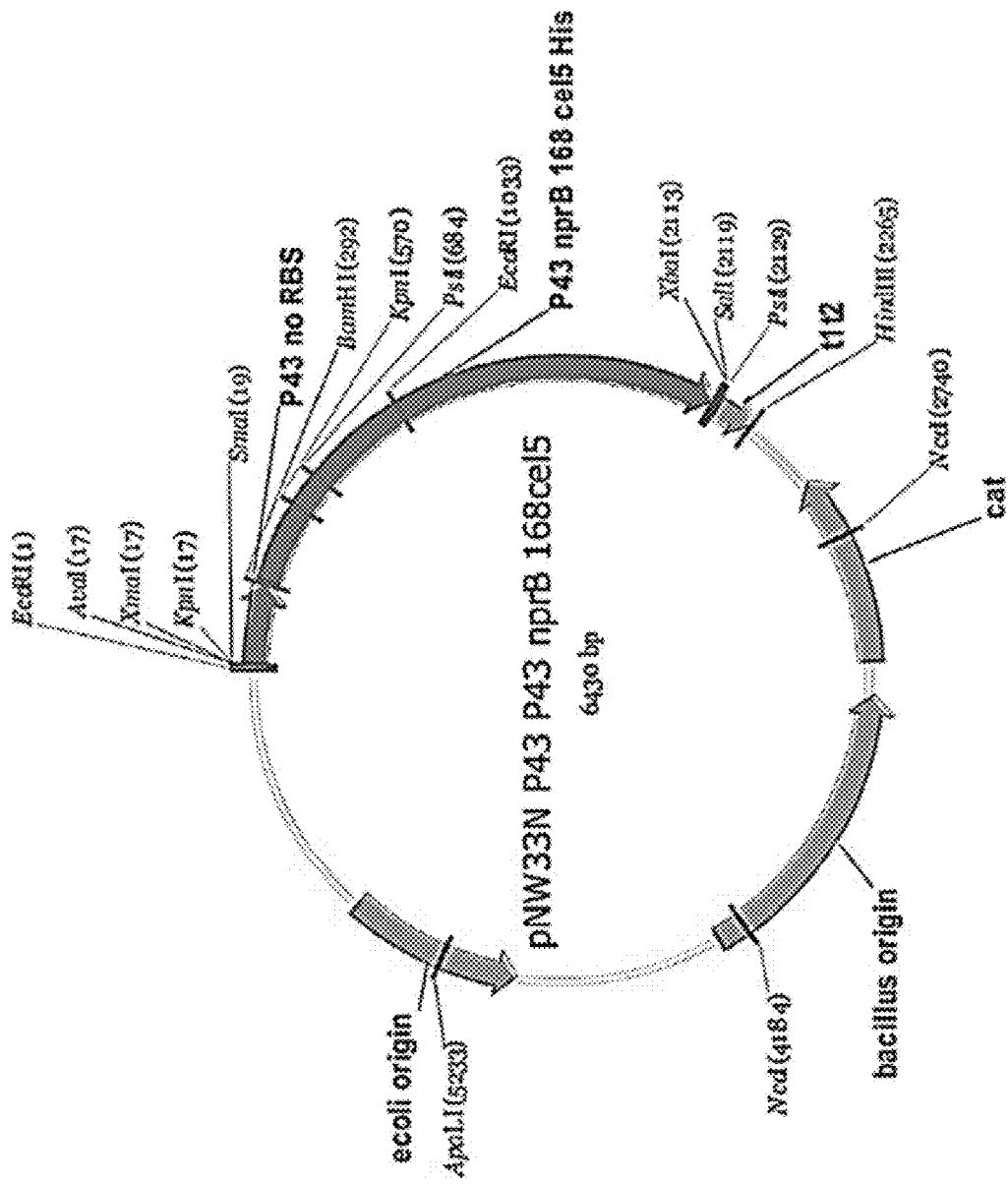
FIG. 12 shows the schematic structure of a vector (pNW33N P43 P43 nprB 168cel5) for expressing saccharifying enzymes using the promoters designed in FIG. 11a and FIG. 11b according to an exemplary embodiment of the present disclosure.

Of the two promoters that showed strong gene expression, the P43 P43 promoter (SEQ ID NO 5) used to prepare a cellulase expression vector as shown in FIG. 12. After inserting the P43 promoter into the pNW33N vector, which is a shuttle vector for *E. coli* and *Bacillus*, the P43 promoter, a signal peptide (nprB) and cellulase (cel5) were cloned into the pNW33N P43 vector by overlap PCR. The promoter (P43) cellulase (cel5) and the signal peptide (nprB) were amplified by PCR using the genomic DNA of *Bacillus subtilis* 168 as a template. The amplified PCR products were amplified by overlap PCR to obtain P43-nprB-cel5.

After ligating the pNW33N vector with P43 by treating with SmaI and BamHI and transforming into *E. coli* DH5a, followed by plating on an LB agar plate containing 25 μg/mL Cm, the pNW33N-P43 recombinant plasmid was identified by colony inoculation.

After ligating the prepared pNW33N-P43 vector with P43-nprB-cel5 by treating with BamHI and XbaI and transforming into *E. coli* DH5a, followed by plating on an LB agar plate containing 25 μg/mL Cm, the pNW33N-P43-P43 nprB cel5 recombinant plasmid (SEQ ID NO 6) was identified by colony inoculation.

Preparation of Genetically Engineered Strain of *Paenibacillus* sp. CAA11

After transforming *Paenibacillus* sp. CAA11 by introducing the prepared recombinant vector, a genetically engineered strain of *Paenibacillus* sp. CAA11 was prepared by culturing in a medium containing 10 μg/mL Cm.

The transformation was performed as follows.

First, *Paenibacillus* sp. CAA11 was cultured overnight in an LB (Luria-Bertani) medium containing 0.5 M sorbitol at 37° C. and then subcultured in the same medium. The cells were harvested by centrifuging at 6000 rpm for 10 minutes at 4° C. when $OD_{600}$ reached 0.8. After washing 4 times with 30 mL of a cold washing buffer (0.5 M sorbitol, 0.5 M mannitol, 0.25 mM $KH_2PO_4$, 0.25 mM $K_2HPO_4$, 0.5 mM $MgCl_2$, 10% glycerol), competent cells were prepared by resuspending in a washing buffer with a volume of 1/40 as compared to that of the culture.

Then, after mixing 300-400 ng of purified plasmid DNA and 60 μL of the cell suspension which had been cooled to a very low temperature and transferring to an electroporation cuvette which had been cooled to a very low temperature, electroporation was conducted under a condition of 21 kV/cm, 200Ω and 25 μF (time constant=5 ms). After mixing 1 mL of an LB, 0.5 M sorbitol, 0.38 M mannitol medium with pulsed cells and culturing them at 37° C. for 3 hours while agitating at 200 rpm, transformation was performed by spreading the cell mixture in a medium containing 10 μg/mL Cm.

Test Example 5

Comparison of Promoter Intensity

Figure 11B:
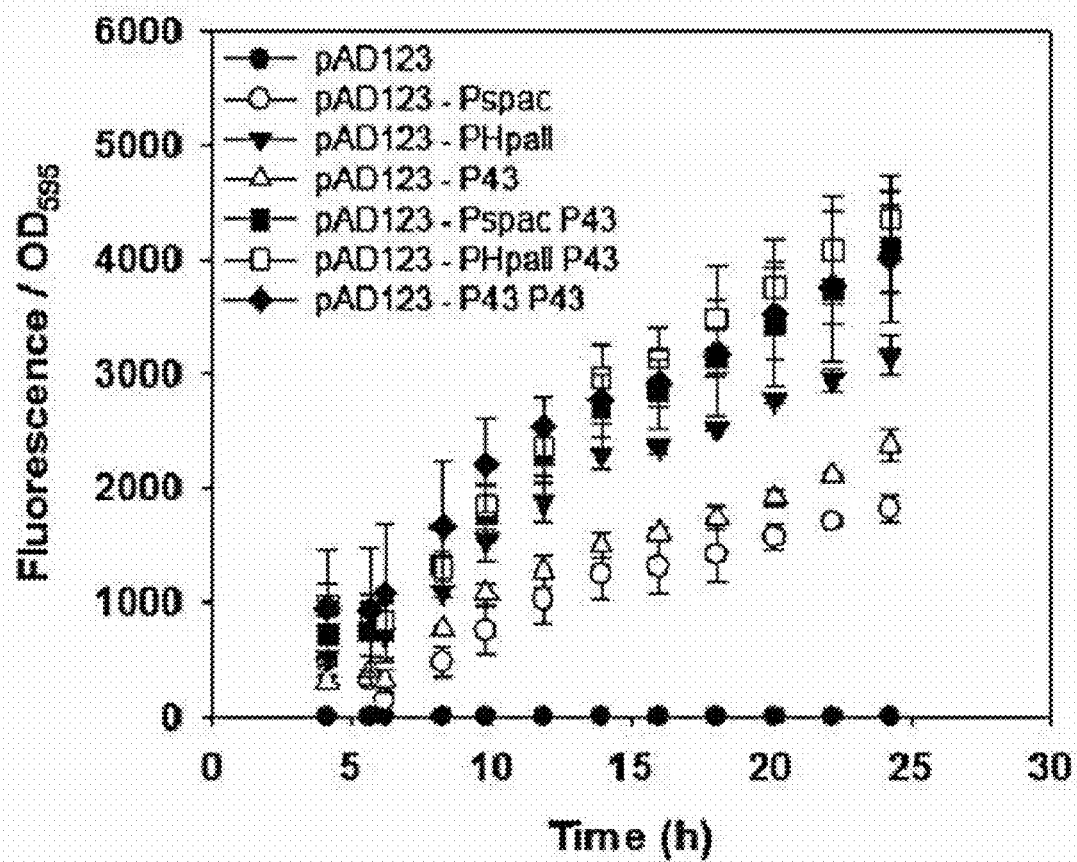

The prepared vector for measuring promoter intensity was introduced into *Bacillus* SPF35 which is similar to *Paenibacillus* sp. CAA11. After culturing in an LB medium containing 5 μg/mL Cm, the completed vector was introduced into *Paenibacillus* sp. CAA11 and promoter intensity was analyzed by measuring the intensity of fluorescence. As seen from FIG. 11b, the fluorescence intensity was stronger when two promoters were inserted in a row than when one promoter was used. Based on the experimental result, two promoters were used to express a target gene in the isolated strain.

Test Example 6

Comparison of Cellulose-Degrading Ability of Genetically Engineered Strain of *Paenibacillus* sp. CAA11 in Solid Medium Based on the result of [Test Example 5], a pNW33N-P43 P43-nprB cel5 vector wherein two promoters are connected in series was prepared (FIG. 12). After transforming into CAA11, improvement in the cellulose-degrading ability of the recombinant strain was compared with that of a control group which has been transformed by an empty vector.

Figure 13:
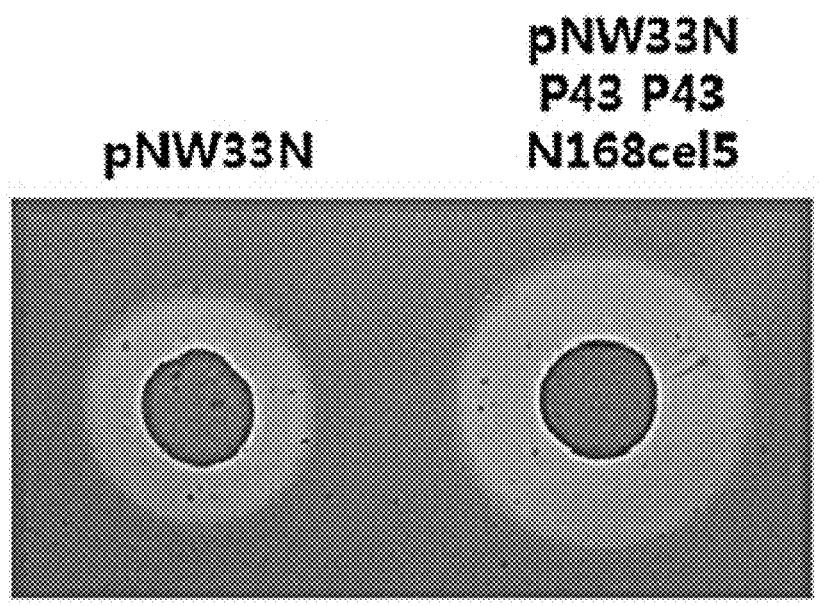
FIG. 13 shows enhancement of saccharifying enzyme activity by a genetically engineered strain of *Paenibacillus* sp. CAA11.
Figure 14A:
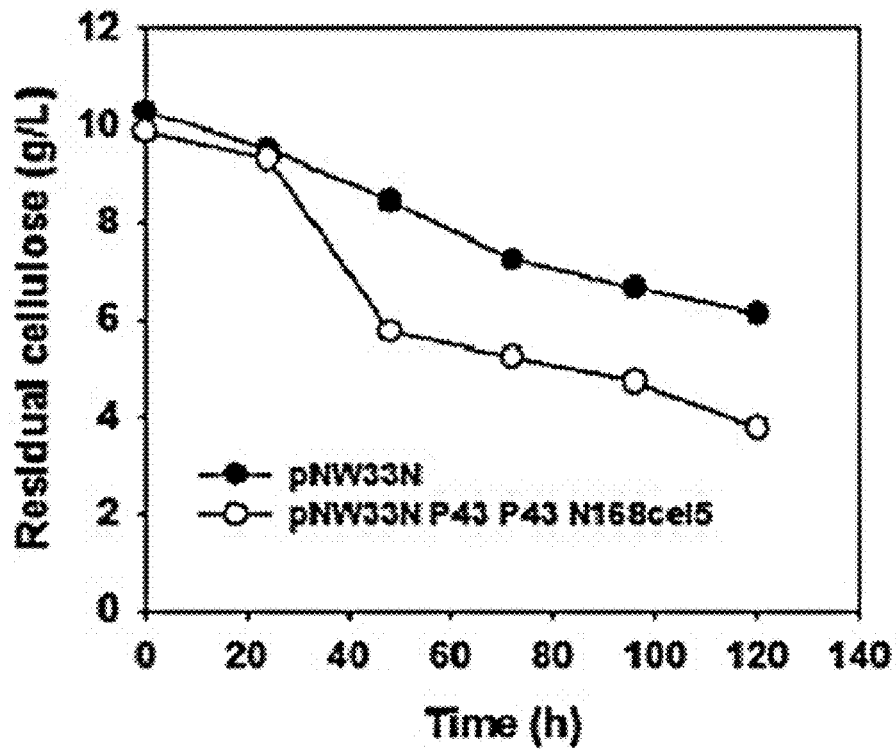
FIGS. 14a-14e show a result of analyzing products produced when a genetically engineered strain of *Paenibacillus* sp. CAA11 is cultured in a cellulose medium.
Figure 14B:
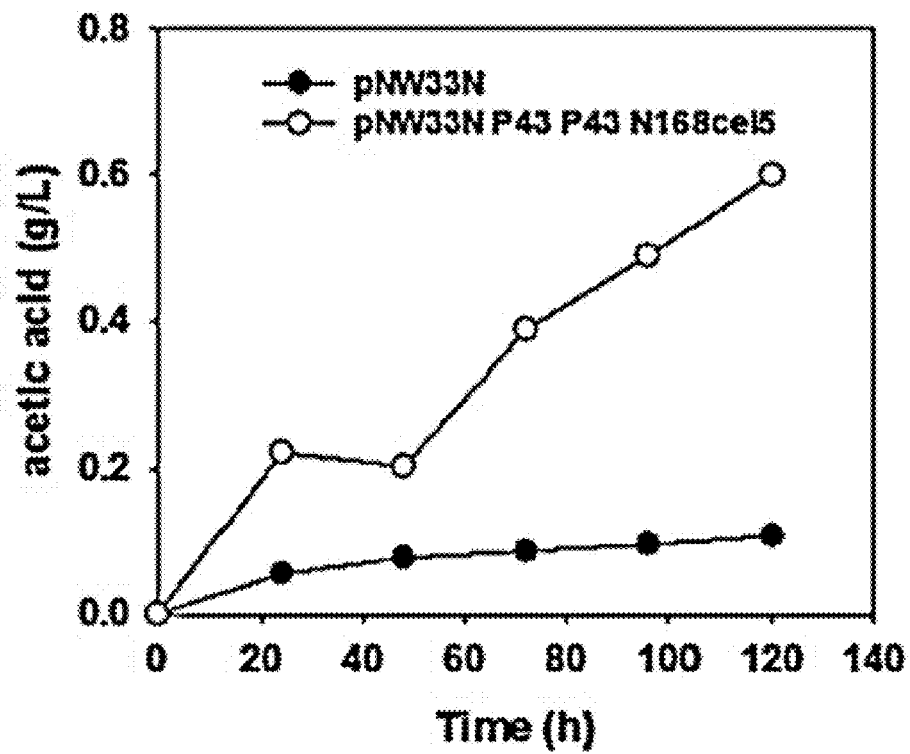
Figure 14C:
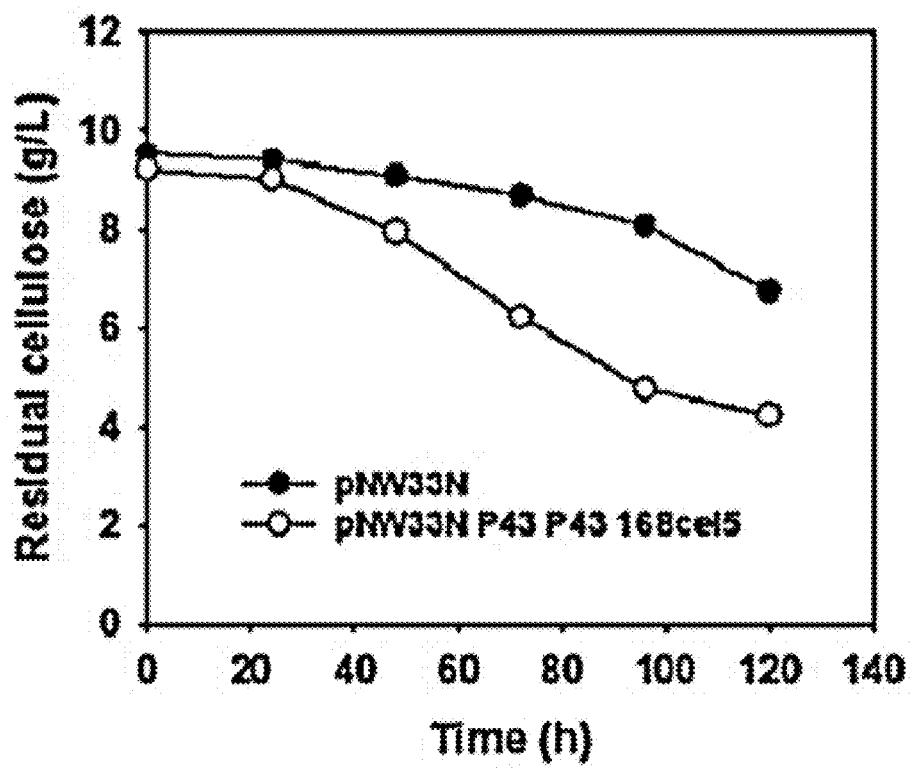
Figure 14D:
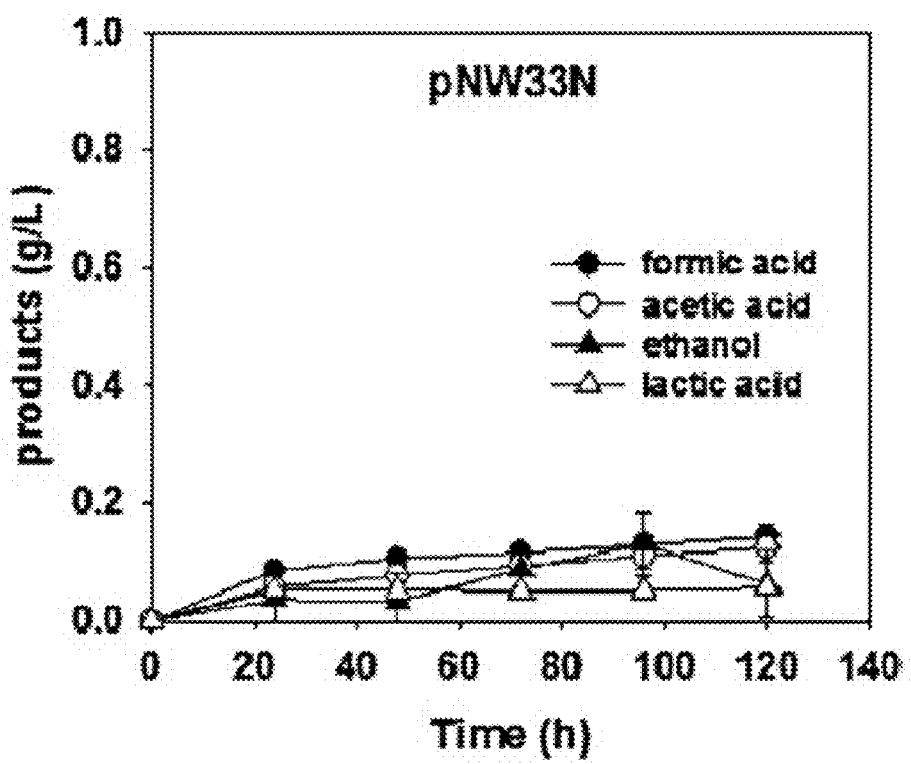
Figure 14E:
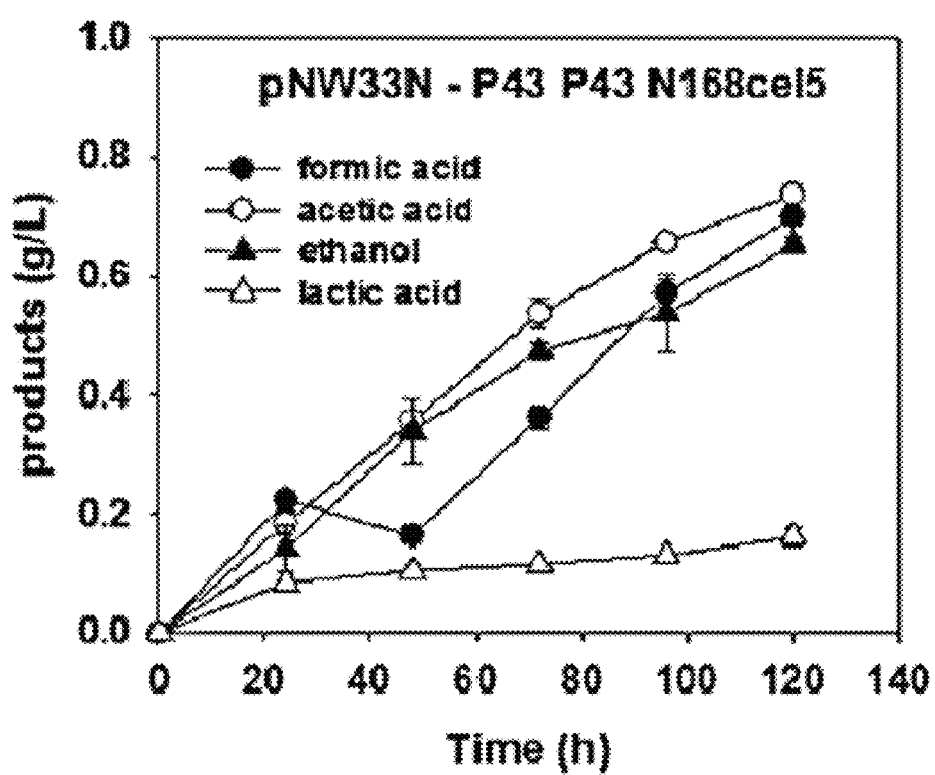

First, after culturing *Paenibacillus* sp. CAA11 containing only an empty vector or *Paenibacillus* sp. CAA11 containing a cellulase overexpression vector in M9 medium containing 10 g/L carboxymethyl cellulose (CMC) as a soluble cellulose in a liquid solution for 24 hours, followed by staining with a 0.1% Congo red solution which is capable of analyzing the degree of cellulose degradation and destaining with 1 M NaCl, the size of the halo zone where cellulose had been degraded was compared. From FIG. 13, it can be seen that the cellulase-overexpressing strain has improved cellulose-degrading ability.

Test Example 7

Analysis of Cellulose-Degrading Ability of Genetically Engineered Strain of *Paenibacillus* sp. CAA11 and Produced Products in Liquid Medium The cellulose-degrading ability of the cellulase-overexpressing strain and the produced products were analyzed while culturing in a cellulose medium. The cellulose (RAC; regenerated amorphous cellulose) used in the medium was prepared as follows. 10 g of crystalline cellulose Avicel PH-101 was mixed with 100 mL of 85% phosphoric acid and treated at 50° C. for 6 hours. After washing 4 times with sterilized distilled water and allowing to stand overnight at 4° C. after adding 30 mL of 2 N NaOH, the mixture was washed with sterilized distilled water until pH reached ~7.0.

After culturing *Paenibacillus* sp. CAA11 overnight in M9 medium containing 5 g/L glucose and transferring to 50 mL of M9 medium containing 5 g/L glucose, the strain was cultured in aerobic and anaerobic conditions at 37° C. while agitating at 200 rpm.

1.5-mL samples were taken with 24-hour intervals. After centrifuging 1 mL of the sample at 13000 rpm for 10 minutes, products were analyzed from the supernatant and the pellets were used for quantification of cellulose. The products were analyzed by HPLC (Agilent 1260 (Waldbronn, Germany), refractive index detector (RID); Aminex HPX-87 H ion exclusion column (300 mm×7.8 mm, Bio-Rad, Hercules, Calif., USA)).

In order to remove the cultured cells from the cellulose obtained as the pellets, the pellets were incubated at 37° C. for 30 minutes after adding 40 µg/mL lysozyme. Then, the pellets were incubated at room temperature for 30 minutes after adding 20 µL of BugBuster reagent (Novagen). After washing 2 times with distilled water and diluting to 1/10, 10 µL of the sample was incubated for 30 minutes at room temperature on a 96-well plate after adding 200 µL of a sulfuric acid solution and 20 µL of a 5% phenol solution. The quantity of cellulose remaining in the culture was determined by measuring absorbance at 490 nm.

The result of culturing the strain with improved cellulose-degrading ability in M9 medium containing 10 g/L RAC and 1 g/L yeast extract in aerobic and anaerobic conditions is shown in FIGS. 14a-14e. In aerobic condition, the control group containing the empty vector degraded 41% of cellulose and produced 0.11 g/L acetic acid. The strain with improved cellulose-degrading ability degraded 62% of cellulose and produced 0.6 g/L acetic acid. In anaerobic condition, the control group degraded 30% of cellulose and produced 0.14 g/L formic acid, 0.12 g/L acetic acid, 0.13 g/L ethanol and 0.06 g/L lactic acid. The strain with improved cellulose-degrading ability degraded 54% of cellulose and produced 0.7 g/L formic acid, 0.74 g/L acetic acid, 0.65 g/L ethanol and 0.16 g/L lactic acid.

It was confirmed that *Paenibacillus* sp. CAA11 can degrade cellulose both in aerobic and anaerobic conditions, and can produce acetic acid in aerobic condition and acetic acid, formic acid, ethanol and lactic acid in anaerobic condition. It was also confirmed that the genetically engineered strain of *Paenibacillus* sp. CAA11 whose cellulose-degrading ability was improved through overexpression of cel5 degrades cellulose better and produces about 5-6 times more products as compared to the non-transformed *Paenibacillus* sp. CAA11.

While the exemplary embodiments have been shown and described, it will be understood by those skilled in the art that various changes in form and details may be made thereto without departing from the spirit and scope of the present disclosure as defined by the appended claims.

Accession Number 1
Depository agency: Korean Culture Center of Microorganisms.
Accession number: KCCM 11602P.
Date of accession: Nov. 6, 2014.
Accession Number 2
Depository agency: Korean Culture Center of Microorganisms.
Accession number: KCCM 11825P.
Date of accession: Mar. 24, 2016

What is claimed is:

1. A bacterial cell of *Paenibacillus* sp. CAA11, deposition number of KCCM 11602P.

2. A genetically engineered bacterial cell of *Paenibacillus* sp. CAA11-Cel, transformed by expressing a *Bacillus subtilis* 168 cellulase gene in a *Paenibacillus* sp. CAA11 cell of claim 1.

3. The genetically engineered bacterial cell of *Paenibacillus* sp. CAA11-Cel according to claim 2, with a deposition number of KCCM11825P.

4. The genetically engineered bacterial cell of *Paenibacillus* sp. CAA11-Cel according to claim 2, wherein the *Bacillus subtilis* 168 cellulase gene has a nucleotide sequence of SEQ ID NO 4.

5. The genetically engineered bacterial cell of *Paenibacillus* sp. CAA11-Cel according to claim 2, wherein the vector comprises a promoter having a nucleotide sequence of SEQ ID NO 5 upstream of the *Bacillus subtilis* 168 cellulase gene.

6. The genetically engineered bacterial cell of *Paenibacillus* sp. CAA11-Cel according to claim 2, wherein the vector has a nucleotide sequence of SEQ ID NO 6.

7. A method for preparing the genetically engineered bacterial cell of *Paenibacillus* sp. CAA11-Cel according to claim 2, the method comprising:
   preparing an expression vector by inserting a promoter into a shuttle vector;
   preparing a recombinant vector by joining the promoter with a signal peptide and a cellulase-encoding gene by inserting them into the expression vector by overlap PCR and cloning the same; and
   transforming the recombinant vector into a bacterial cell of *Paenibacillus* sp. CAA11.

8. The method according to claim 7, wherein the transforming further comprises performing electroporation.

9. A culture comprising bacterial cells of *Paenibacillus* sp. CAA11 according to claim 1.

10. A culture comprising bacterial cells of *Paenibacillus* sp. CAA11-Cel according to claim 2.

11. A culturing method comprising:
    culturing the bacterial cells of *Paenibacillus* sp. CAA11-Cel according to claim 2 in presence of lignocellulosic biomass or cellulose.

12. The culturing method according to claim 11, wherein the culturing the bacterial cells of *Paenibacillus* sp. CAA11-Cel is in aerobic or anaerobic condition.

13. A method of producing a fermentation product, the method comprising
    culturing the bacterial cells of *Paenibacillus* sp. CAA11-Cel according to claim 2 in presence of lignocellulosic biomass or cellulose and aerobic or anaerobic condition; and
    obtaining a fermentation product from a culture obtained by culturing the bacterial cells of *Paenibacillus* sp. CAA11-Cel.

14. The method of producing a fermentation product according to claim 13, wherein the culturing of the bacterial cells of *Paenibacillus* sp. CAA11-Cel is in presence of lignocellulosic biomass or cellulose.

15. The method of producing a fermentation product according to claim 14, further comprising:
    producing one or more of glucose, xylose and cellobiose by degrading lignocellulosic biomass or cellulose with the bacterial cells of *Paenibacillus* sp. CAA11-Cel; and
    culturing the bacterial cells of *Paenibacillus* sp. CAA11-Cel using one or more of the produced glucose, xylose and cellobiose.

16. The method of producing a fermentation product according to claim 13, wherein the fermentation product comprises one or more selected from a group consisting of formic acid, acetic acid and ethanol.

17. A method of producing biofuel, the method comprising:
    culturing the bacterial cells of *Paenibacillus* sp. CAA11-Cel according to claim 2 in presence of lignocellulosic biomass or cellulose; and
    producing biofuel by using a byproduct obtained during the culturing,
    wherein the byproduct comprises one or more selected from a group consisting of acetic acid, formic acid and ethanol.

18. A culturing method comprising culturing the bacterial cells of *Paenibacillus* sp. CAA11 according to claim 1 in presence of lignocellulosic biomass or cellulose.

19. A method of producing a fermentation product, the method comprising:

culturing the bacterial cells of *Paenibacillus* sp. CAA11 according to claim 1 in presence of lignocellulosic biomass or cellulose; and obtaining a fermentation product from a culture obtained by culturing the bacterial cells of *Paenibacillus* sp. CAA11.

20. A method of producing biofuel, the method comprising:

culturing the bacterial cells of *Paenibacillus* sp. CAA11 according to claim 1 in presence of lignocellulosic biomass or cellulose; and producing biofuel by using a byproduct obtained during the culturing, wherein the byproduct comprises one or more selected from a group consisting of acetic acid, formic acid and ethanol.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: forward primer for amplifying strain of Example
      1-1

<400> SEQUENCE: 1
agagtttgat ctgctcag                                                  18

<210> SEQ ID NO 2
<211> LENGTH: 20
```

```
<212> TYPE: DNA
<213> ORGANISM: Artificial Sequence
<220> FEATURE:
<223> OTHER INFORMATION: reverse primer for amplifying strain of Example
      1-1

<400> SEQUENCE: 2
aaggaggtga tccagccgca                                                20

<210> SEQ ID NO 3
<211> LENGTH: 1437
<212> TYPE: DNA
<213> ORGANISM: Artificial Sequence
<220> FEATURE:
<223> OTHER INFORMATION: Sequence of amplified strain of Example 1-1

<400> SEQUENCE: 3
ctatactgca gtcgagcgga gttatttaga agcttgcttc taaataactt agcggcggac      60
gggtgagtaa cacgtaggca acctgcctgt aagactggga taactaccgg aaacggtagc     120
taataccgga tacacaagtt cctcgcatga gggatttggg aaagacggag caatctgtca     180
cttacggatg ggcctgcggc gcattagcta gttggtgggg taacggctca ccaaggcgac     240
gatgcgtagc cgacctgaga gggtgaacgg ccacactggg actgagacac ggcccagact     300
cctacgggag gcagcagtag ggaatcttcc gcaatggacg aaagtctgac ggagcaacgc     360
cgcgtgagtg atgaaggttt tcggatcgta aagctctgtt gccagggaag aacgcttgag     420
agagtaactg ctcttaaggt gacggtacct gagaagaaag ccccggctaa ctacgtgcca     480
gcagccgcgg taatacgtag ggggcaagcg ttgtccggaa ttattgggcg taaagcgcgc     540
gcaggcggcc atttaagtct ggtgtttaat cctggagctc aactccgggt cgcactggaa     600
actgggtggc ttgagtgcag aagaggagag tggaattcca cgtgtagcgg tgaaatgcgt     660
agagatgtgg aggaacacca gtggcgaagg cgactctctg gctgtaact  gacgctgagg     720 cgcgaaagcg tggggagcaa acaggattag ataccctggt agtccacgcc gtaaacgatg     780
aatgctaggt gttaggggtt tcgatacct  tggtgccgaa gttaacacat taagcattcc     840
gcctggggag tacggtcgca agactgaaac tcaaaggaat tgacggggac ccgcacaagc     900
agtggagtat tgtggtttaa ttcgaagcaa cgcgaagaac cttaccaggt cttgacatcc     960
ctctgaccgg tacagagatg tacctttcct ttacggacaa aggaaacagg tgggtgcatg    1020
gttgtcgtca gctcgtgtcg tgagatgttg ggttaagtcc cgcaacgagc gcaacccta    1080 actttagttg ccagcaggtc aagctgggca ctctagagtg actgccggtg acaaaccgga    1140
ggaaggtggg gatgacgtca atcatcatg ccccttatga cctgggctac acacgtacta    1200
caatggccgg tacaacggga agcgaaggag cgatctggag cgaatcctag aaaagccggt    1260
ctcagttcgg attgcaggct gcaactcgcc tgcatgaagt cggaattgct agtaatcgcg    1320
gatcagcatg ccgcggtgaa tacgttcccg ggtcttgtac acaccgcccg tcacaccacg    1380
agagtttaca cacccgaag tcggtgaggt aacccgcaag ggggccagcc gccgaag       1437

<210> SEQ ID NO 4
<211> LENGTH: 1410
<212> TYPE: DNA
<213> ORGANISM: Artificial Sequence
<220> FEATURE:
<223> OTHER INFORMATION: sequence of bacillus subtilis 168 cellulase
      (cel5)

<400> SEQUENCE: 4
```

```
gcagggacaa aaacgccagt agccaagaat ggccagctta gcataaaagg tacacagctc    60
gttaaccgag acggtaaagc ggtacagctg aaggggatca gttcacacgg attgcaatgg   120
tatggagaat atgtcaataa agacagctta aaatggctga gagatgattg gggtatcacc   180
gttttccgtg cagcgatgta tacggcagat ggcggttata ttgacaaccc gtccgtgaaa   240
aataaagtaa agaagcggt tgaagcggca aaagagcttg ggatatatgt catcattgac    300
tggcatatct aaatgacgg taatccaaac caaaataaag agaaggcaaa agaattcttc    360
aaggaaatgt caagccttta cggaaacacg ccaaacgtca tttatgaaat tgcaaacgaa   420
ccaaacggtg atgtgaactg gaagcgtgat attaaaccat atgcggaaga agtgatttca   480
gttatccgca aaaatgatcc agacaacatc atcattgtcg gaaccggtac atggagccag   540
gatgtgaatg atgctgccga tgaccagcta aaagatgcaa acgttatgta cgcacttcat   600
ttttatgccg gcacacacgg ccaattttta cgggataaag caaactatgc actcagcaaa   660
ggagcaccta ttttgtgac agagtgggga acaagcgacg cgtctggcaa tggcggtgta   720
ttccttgatc aatcgaggga atggctgaaa tatctcgaca gcaagaccat tagctgggtg   780
aactggaatc tttctgataa gcaggaatca tcctcagctt taaagccggg ggcatctaaa   840
acaggcggct ggcggttgtc agatttatct gcttcaggaa cattcgttag agaaaacatt   900
ctcggcacca agattcgac gaaggacatt cctgaaacgc catcaaaaga taaacccaca    960
caggaaaatg gtatttctgt acagtacaga gcagggatg ggagtatgaa cagcaaccaa   1020
atccgtccgc agcttcaaat aaaaaataac ggcaatacca cggttgattt aaaagatgtc  1080
actgcccgtt actggtataa agcgaaaaac aaaggccaaa actttgactg tgactacgcg  1140
cagattggat gcggcaatgt gacacacaag tttgtgacgt tgcataaacc aaagcaaggt  1200
gcagatacct atctggaact tggatttaaa acggaacgt tggcaccggg agcaagcaca   1260
gggaatattc agctccgtct tcacaatgat gactggagca attatgcaca aagcggcgat  1320
tattcctttt tcaaatcaaa tacgtttaaa acaacgaaaa aaatcacatt atatgatcaa  1380
ggaaaactga tttggggaac agaaccaaat                                   1410

<210> SEQ ID NO 5
<211> LENGTH: 542
<212> TYPE: DNA
<213> ORGANISM: Artificial Sequence
<220> FEATURE:
<223> OTHER INFORMATION: sequence of promoter P43 P43

<400> SEQUENCE: 5
tgataggtgg tatgttttcg cttgaacttt taaatacagc cattgaacat acggttgatt    60
taataactga caaacatcac cctcttgcta aagcggccaa ggacgctgcc gccggggctg   120
tttgcgtttt tgccgtgatt tcgtgtatca ttggtttact tatttttttg ccaaagctgt   180
aatggctgaa aattcttaca tttattttac attttttagaa atgggcgtga aaaaagcgc   240 gcgattatgt aaaatataaa gtgatagcgg atcctgatag gtggtatgtt ttcgcttgaa   300
cttttaaata cagccattga acatacggtt gatttaataa ctgacaaaca tcaccctctt   360
gctaaagcgg ccaaggacgc tgccgccggg gctgtttgcg ttttttgccgt gatttcgtgt  420 atcattggtt tacttatttt tttgccaaag ctgtaatggc tgaaaattct tacatttatt   480
ttacattttt tagaaatggg cgtgaaaaaaa gcgcgcgatt atgtaaaata taaagtgata  540
gc                                                                  542
```

<210> SEQ ID NO 6
<211> LENGTH: 6291
<212> TYPE: DNA
<213> ORGANISM: Artificial Sequence
<220> FEATURE:
<223> OTHER INFORMATION: sequence of vector pNW33N-P43-P43 nprB cel5

<400> SEQUENCE: 6

| | | | | | | |
|---|---|---|---|---|---|---|
| aattcgagct | ctgataggtg | gtatgttttc | gcttgaactt | ttaaatacag | ccattgaaca | 60 |
| tacggttgat | ttaataactg | acaaacatca | ccctcttgct | aaagcggcca | aggacgctgc | 120 |
| cgccggggct | gtttgcgttt | ttgccgtgat | ttcgtgtatc | attggtttac | ttattttttt | 180 |
| gccaaagctg | taatggctga | aaattcttac | atttatttta | catttttaga | aatgggcgtg | 240 |
| aaaaaaagcg | cgcgattatg | taaaatataa | agtgatagcg | gatcctgata | ggtggtatgt | 300 |
| tttcgcttga | acttttaaat | acagccattg | aacatacggt | tgatttaata | actgacaaac | 360 |
| atcaccctct | tgctaaagcg | gccaaggacg | ctgccgccgg | ggctgtttgc | gttttgccg | 420 |
| tgatttcgtg | tatcattggt | ttacttattt | ttttgccaaa | gctgtaatgg | ctgaaaattc | 480 |
| ttacatttat | tttacatttt | tagaaatggg | cgtgaaaaaa | agcgcgcgat | tatgtaaaat | 540 |
| ataaagtgat | agcggtacca | ttataggtaa | gagaggaatg | tacacatgcg | caacttgacc | 600 |
| aagacatctc | tattactggc | cggcttatgc | atagcggccc | aaatggtttt | tgtaacacat | 660 |
| gccccagctg | cagggacaaa | aacgccagta | gccaagaatg | gccagcttag | cataaaaggt | 720 |
| acacagctcg | ttaaccgaga | cggtaaagcg | gtacagctga | aggggatcag | ttcacacgga | 780 |
| ttgcaatggt | atgagaata | tgtcaataaa | gacagcttaa | aatggctgag | agatgattgg | 840 |
| ggtatcaccg | ttttccgtgc | agcgatgtat | acggcagatg | gcggttatat | tgacaacccg | 900 |
| tccgtgaaaa | ataaagtaaa | agaagcggtt | gaagcggcaa | aagagcttgg | gatatatgtc | 960 |
| atcattgact | ggcatatctt | aaatgacggt | aatccaaacc | aaaataaaga | gaaggcaaaa | 1020 |
| gaattcttca | aggaaatgtc | aagcctttac | ggaaacacgc | caaacgtcat | ttatgaaatt | 1080 |
| gcaaacgaac | caaacggtga | tgtgaactgg | aagcgtgata | ttaaaccata | tgcggaagaa | 1140 |
| gtgatttcag | ttatccgcaa | aaatgatcca | gacaacatca | tcattgtcgg | aaccggtaca | 1200 |
| tggagccagg | atgtgaatga | tgctgccgat | gaccagctaa | aagatgcaaa | cgttatgtac | 1260 |
| gcacttcatt | tttatgccgg | cacacacggc | caattttac | gggataaagc | aaactatgca | 1320 |
| ctcagcaaag | gagcacctat | ttttgtgaca | gagtggggaa | caagcgacgc | gtctggcaat | 1380 |
| ggcggtgtat | tccttgatca | atcgagggaa | tggctgaaat | atctcgacag | caagaccatt | 1440 |
| agctgggtga | actggaatct | ttctgataag | caggaatcat | cctcagcttt | aaagccgggg | 1500 |
| gcatctaaaa | caggcggctg | gcggttgtca | gatttatctg | cttcaggaac | attcgttaga | 1560 |
| gaaacattc | tcggcaccaa | agattcgacg | aaggacattc | ctgaaacgcc | atcaaaagat | 1620 |
| aaacccacac | aggaaaatgg | tatttctgta | cagtacagag | caggggatgg | gagtatgaac | 1680 |
| agcaaccaaa | tccgtccgca | gcttcaaata | aaaataacg | gcaataccac | ggttgattta | 1740 |
| aaagatgtca | ctgcccgtta | ctggtataaa | gcgaaaaaca | aaggccaaaa | ctttgactgt | 1800 |
| gactacgcgc | agattggatg | cggcaatgtg | acacacaagt | tgtgacgtt | gcataaacca | 1860 |
| aagcaaggtg | cagataccta | tctggaactt | ggatttaaaa | acggaacgtt | ggcaccggga | 1920 |
| gcaagcacag | ggaatattca | gctccgtctt | cacaatgatg | actggagcaa | ttatgcacaa | 1980 |
| agcggcgatt | attcctttt | caaatcaaat | acgtttaaaa | caacgaaaaa | aatcacatta | 2040 |
| tatgatcaag | gaaaactgat | tgggggaaca | gaaccaaatc | atcatcatca | tcatcattag | 2100 |

```
tctagagtcg acctgcaggc atgcaagctt ggcgtaatca tggtcatagc tgtttcctgt    2160
gtgaaattgt tatccgctca caattccaca acatacga gccggaagca taaagtgtaa      2220
agcctggggt gcctaatgag tgagctaact cacattaatt gcgttgcgct cactgcccgc    2280
tttccagtcg ggaaacctgt cgtgccagcc cttcaaactt cccaaaggcg agccctagtg    2340
acattagaaa accgactgta aaagtacag tcggcattat ctcatattat aaaagccagt    2400
cattaggcct atctgacaat tcctgaatag agttcataaa caatcctgca tgataaccat    2460
cacaaacaga atgatgtacc tgtaaagata gcggtaaata tattgaatta cctttattaa    2520
tgaattttcc tgctgtaata atgggtagaa ggtaattact attattattg atatttaagt    2580
taaacccagt aaatgaagtc catggaataa tagaaagaga aaaagcattt tcaggtatag    2640
gtgttttggg aaacaatttc cccgaaccat tatatttctc tacatcagaa aggtataaat    2700
cataaaactc tttgaagtca ttcttttacag gagtccaaat accagagaat gttttagata   2760
caccatcaaa aattgtataa agtggctcta acttatccca ataacctaac tctccgtcgc    2820
tattgtaacc agttctaaaa gctgtatttg agtttatcac ccttgtcact aagaaaataa    2880
atgcagggta aaatttatat ccttcttgtt ttatgtttcg gtataaaaca ctaatatcaa    2940
tttctgtggt tatactaaaa gtcgtttgtt ggttcaaata atgattaaat atctctttttc   3000
tcttccaatt gtctaaatca attttattaa agttcatttg atatgcctcc taaattttta    3060
tctaaagtga atttaggagg cttacttgtc tgctttcttc attagaatca atcctttttt    3120
aaaagtcaat cccgtttgtt gaactactct ttaataaaat aattttttccg ttcccaattc   3180
cacattgcaa taatagaaaa tccatcttca tcggcttttt cgtcatcatc tgtatgaatc    3240
aaatcgcctt cttctgtgtc atcaaggttt aattttttat gtatttcttt taacaaacca    3300
ccataggaga ttaacctttt acggtgtaaa ccttcctcca aatcagacaa acgtttcaaa    3360
ttcttttctt catcatcggt cataaaatcc gtatcctta caggatattt tgcagtttcg    3420
tcaattgccg attgtatatc cgatttatat ttatttttcg gtcgaatcat ttgaactttt    3480
acatttggat catagtctaa tttcattgcc ttttccaaa attgaatcca ttgttttga    3540
ttcacgtagt tttctgtatt cttaaaataa gttggttcca cacataccaa tacatgcatg    3600
tgctgattat aagaattatc tttattattt attgtcactt ccgttgcacg cataaaacca    3660
acaagatttt tattaatttt tttatattgc atcattcggc gaaatccttg agccatatct    3720
gacaaactct tatttaattc ttcgccatca taaacatttt taactgttaa tgtgagaaac    3780
aaccaacgaa ctgttggctt ttgtttaata acttcagcaa caaccttttg tgactgaatg    3840
ccatgtttca ttgctctcct ccagttgcac attggacaaa gcctggattt acaaaaccac    3900
actcgataca actttctttc gcctgtttca cgatttttgtt tatactctaa tatttcagca   3960
caatctttta ctcttttcagc cttttttaaat tcaagaatat gcagaagttc aaagtaatca    4020
acattagcga ttttctttc tctccatggt ctcacttttc cacttttttgt cttgtccact    4080
aaaacccttg atttttcatc tgaataaatg ctactattag gacacataat attaaaagaa    4140
accccatct atttagttat ttgtttggtc acttataact ttaacagatg gggttttttct   4200
gtgcaaccaa ttttaagggt tttcaatact ttaaaacaca tacataccaa cacttcaacg    4260
cacctttcag caactaaaat aaaaatgacg ttatttctat atgtatcaag aatagaaaga    4320
actcgttttt cgctacgctc aaaacgcaaa aaaagcactc attcgagtgc ttttttcttat   4380
cgctccaaat catgcgattt tttcctcttt gcttttcttt gctcacgaag ttctcgatca    4440
cgctgcaaaa catcttgaag cgaaaaagta ttcttctttt cttccgatcg ctcatgctga    4500
```

| | |
|---|---|
| cgcacgaaaa gccctctagg cgcataggaa caactcctaa atgcatgtga ggggttttct | 4560 |
| cgtccatgtg aacagtcgca tacgcaatat tttgtttccc atactgcatt aatgaatcgg | 4620 |
| ccaacgcgcg gggagaggcg gtttgcgtat tgggcgctct tccgcttcct cgctcactga | 4680 |
| ctcgctgcgc tcggtcgttc ggctgcggcg agcggtatca gctcactcaa aggcggtaat | 4740 |
| acggttatcc acagaatcag gggataacgc aggaaagaac atgtgagcaa aaggccagca | 4800 |
| aaaggccagg aaccgtaaaa aggccgcgtt gctggcgttt ttccataggc tccgcccccc | 4860 |
| tgacgagcat cacaaaaatc gacgctcaag tcagaggtgg cgaaacccga caggactata | 4920 |
| aagataccag gcgtttcccc ctggaagctc cctcgtgcgc tctcctgttc cgaccctgcc | 4980 |
| gcttaccgga tacctgtccg cctttctccc ttcgggaagc gtggcgcttt ctcatagctc | 5040 |
| acgctgtagg tatctcagtt cggtgtaggt cgttcgctcc aagctgggct gtgtgcacga | 5100 |
| accccccgtt cagcccgacc gctgcgcctt atccggtaac tatcgtcttg agtccaaccc | 5160 |
| ggtaagacac gacttatcgc cactggcagc agccactggt aacaggatta gcagagcgag | 5220 |
| gtatgtaggc ggtgctacag agttcttgaa gtggtggcct aactacggct acactagaag | 5280 |
| aacagtattt ggtatctgcg ctctgctgaa gccagttacc ttcggaaaaa gagttggtag | 5340 |
| ctcttgatcc ggcaaacaaa ccaccgctgg tagcggtggt ttttttgttt gcaagcagca | 5400 |
| gattacgcgc agaaaaaaag gatctcaaga agatcctttg atcttttcta cggggtctga | 5460 |
| cgctcagtgg aacgaaaact cacgttaagg gattttggtc atgagattat caaaaaggat | 5520 |
| cttcacctag atccttttaa attaaaaatg aagttttaaa tcaatctaaa gtatatatga | 5580 |
| gtaaacttgg tctgacagtt accaatgctt aatcagtgag gcacctatct cagcgatctg | 5640 |
| tctatttcgt tcatccatag ttgcctgact ccccgtcgtg tagataacta cgatacggga | 5700 |
| gggcttacca tctggcccca gtgctgcaat gataccgcga cccacgct caccggctcc | 5760 |
| agatttatca gcaataaacc agccagcccg atatgggaaa caaatattg cgtatgcgac | 5820 |
| tgttcacatg gacgagaaaa cccctcacat gcatttagga gttgttccta tgcgcctaga | 5880 |
| gggcttttcg tgcgtcagca tgagcgatcg gaagaaaaga agaatacttt ttcgcttcaa | 5940 |
| gatgttttgc agcgtgatcg agaacttcgt gagcaaagaa aagcaaagag gaaaaaatcg | 6000 |
| catgatttgg agcgataaga aaaagcactc gaatgagtgc tttttttgcg ttttgagcgt | 6060 |
| agcgaaaaac gagttctttc tattcttgat acatatagaa ataacgtcat ttttattta | 6120 |
| gttgctgaaa ggtgcgttga agtgttggta tgtatgtgat tcaataattt cttttactcg | 6180 |
| ctcgttatag tcgatcggtt catcattcac caaatcataa ttttcatgtg accgttcttt | 6240 |
| atcaatatcg ggattcgttt tactttcccg ttctctctga ttgtgaaatt g | 6291 |

<210> SEQ ID NO 7
<211> LENGTH: 304
<212> TYPE: DNA
<213> ORGANISM: Artificial Sequence
<220> FEATURE:
<223> OTHER INFORMATION: sequence of promoter Pspac

<400> SEQUENCE: 7

| | |
|---|---|
| aggccttaca cagcccagtc cagactattc ggcactgaaa ttatgggtga agtggtcaag | 60 |
| acctcactag gcaccttaaa aatagcgcac cctgaagaag atttatttga ggtagccctt | 120 |
| gcctacctag cttccaagaa agatatccta acagcacaag agcggaaaga tgttttgttc | 180 |
| tacatccaga acaacctctg ctaaaattcc tgaaaaattt tgcaaaaagt tgttgacttt | 240 |

```
atctacaagg tgtggcataa tgtgtggaat tgtgagcgga taacaattaa gcttaaggag      300
gtga                                                                  304

<210> SEQ ID NO 8
<211> LENGTH: 287
<212> TYPE: DNA
<213> ORGANISM: Artificial Sequence
<220> FEATURE:
<223> OTHER INFORMATION: sequence of promoter PHpaII

<400> SEQUENCE: 8
gatcttctca aaaatacta cctgtcccctt gctgattttt aaacgagcac gagagcaaaa        60 ccccccttttg ctgaggtggc agagggcagg tttttttgtt tctttttttct cgtaaaaaaa    120 agaaaggtct taaaggtttt atggttttgg tcggcactgc cgacagcctc gcagagcaca      180
cactttatga atataaagta tagtgtgtta tactttactt ggaagtggtt gccggaaaga      240
gcgaaaatgc ctcacatttg tgccacctaa aaaggagcga tttacat                    287

<210> SEQ ID NO 9
<211> LENGTH: 268
<212> TYPE: DNA
<213> ORGANISM: Artificial Sequence
<220> FEATURE:
<223> OTHER INFORMATION: sequence of promoter P43

<400> SEQUENCE: 9
tgataggtgg tatgttttcg cttgaacttt taaatacagc cattgaacat acggttgatt       60
taataactga caaacatcac cctcttgcta aagcggccaa ggacgctgcc gccggggctg      120
tttgcgtttt tgccgtgatt tcgtgtatca ttggtttact tattttttttg ccaaagctgt    180 aatggctgaa aattcttaca tttatttttac attttttagaa atgggcgtga aaaaaagcgc    240
gcgattatgt aaaatataaa gtgatagc                                         268

<210> SEQ ID NO 10
<211> LENGTH: 578
<212> TYPE: DNA
<213> ORGANISM: Artificial Sequence
<220> FEATURE:
<223> OTHER INFORMATION: sequence of promoter Pspac P43

<400> SEQUENCE: 10
aggccttaca cagcccagtc cagactattc ggcactgaaa ttatgggtga agtggtcaag       60
acctcactag gcaccttaaa aatagcgcac cctgaagaag atttatttga ggtagcccctt    120 gcctacctag cttccaagaa agatatccta acagcacaag agcggaaaga tgttttgttc    180
tacatccaga acaacctctg ctaaaattcc tgaaaaattt tgcaaaaagt tgttgacttt      240
atctacaagg tgtggcataa tgtgtggaat tgtgagcgga taacaattaa gcttaaggag      300
gtgaggatcc tgataggtgg tatgttttcg cttgaacttt taaatacagc cattgaacat      360
acggttgatt taataactga caaacatcac cctcttgcta aagcggccaa ggacgctgcc      420
gccggggctg tttgcgtttt tgccgtgatt tcgtgtatca ttggtttact tattttttttg    480 ccaaagctgt aatggctgaa aattcttaca tttatttttac attttttagaa atgggcgtga   540 aaaaaagcgc gcgattatgt aaaatataaa gtgatagc                              578

<210> SEQ ID NO 11
<211> LENGTH: 561
<212> TYPE: DNA
<213> ORGANISM: Artificial Sequence
```

```
<220> FEATURE:
<223> OTHER INFORMATION: sequence of promoter PHpaII P43

<400> SEQUENCE: 11
gatcttctca aaaatacta cctgtccctt gctgattttt aaacgagcac gagagcaaaa      60
cccccctttg ctgaggtggc agagggcagg ttttttttgtt tctttttttct cgtaaaaaaa     120 agaaaggtct taaaggtttt atggttttgg tcggcactgc cgacagcctc gcagagcaca     180
cactttatga atataaagta tagtgtgtta tactttactt ggaagtggtt gccggaaaga     240
gcgaaaatgc ctcacatttg tgccacctaa aaaggagcga tttacatgga tcctgatagg     300
tggtatgttt tcgcttgaac ttttaaatac agccattgaa catacggttg atttaataac     360
tgacaaacat caccctcttg ctaaagcggc caaggacgct gccgccgggg ctgtttgcgt     420
ttttgccgtg atttcgtgta tcattggttt acttatttt ttgccaaagc tgtaatggct     480
gaaaattctt acatttattt tacattttta gaaatgggcg tgaaaaaaag cgcgcgatta     540
tgtaaaatat aaagtgatag c                                              561
```